US011650314B2

(12) United States Patent
Lee et al.

(10) Patent No.: US 11,650,314 B2
(45) Date of Patent: May 16, 2023

(54) METHOD OF DISPLAYING DOPPLER IMAGE AND ULTRASOUND DIAGNOSIS APPARATUS FOR PERFORMING THE METHOD

(71) Applicant: SAMSUNG MEDISON CO., LTD., Hongcheon-gun (KR)

(72) Inventors: Yujin Lee, Seongnam-si (KR); Jaekeun Lee, Seongnam-si (KR); Hojin Ryoo, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 779 days.

(21) Appl. No.: 16/279,100

(22) Filed: Feb. 19, 2019

(65) Prior Publication Data
US 2019/0257944 A1    Aug. 22, 2019

(30) Foreign Application Priority Data
Feb. 20, 2018    (KR) .................. 10-2018-0020011

(51) Int. Cl.
*A61B 8/06*    (2006.01)
*G01S 15/89*   (2006.01)
(Continued)

(52) U.S. Cl.
CPC ............ *G01S 15/8981* (2013.01); *A61B 8/06* (2013.01); *A61B 8/463* (2013.01); *A61B 8/488* (2013.01);
(Continued)

(58) Field of Classification Search
CPC ............ G01S 15/8981; G01S 7/52077; G01S 7/52079; G01S 15/899; A61B 8/06; A61B 8/463
See application file for complete search history.

(56) References Cited

U.S. PATENT DOCUMENTS 5,782,769 A    7/1998  Hwang et al.
6,402,694 B1   6/2002  Bae et al.
(Continued)

FOREIGN PATENT DOCUMENTS

EP    1 050 761 A2    11/2000
JP    4956210 B2       6/2012
(Continued)

OTHER PUBLICATIONS

Communication dated Jul. 24, 2019, issued by the European Patent Office in counterpart European Application No. 19157553.9.

*Primary Examiner* — Serkan Akar
*Assistant Examiner* — Amal Aly Farag
(74) *Attorney, Agent, or Firm* — Sughrue Mion, PLLC

(57) ABSTRACT

Provided are a method of displaying a Doppler image and an ultrasound diagnosis apparatus for performing the method. The method includes: obtaining a first Doppler signal where clutter filtering corresponding to each of a plurality of pixels is not performed and a second Doppler signal where clutter filtering corresponding to each of the plurality of pixels is performed; determining a first motion score indicating a degree of flash artifact occurrence by using velocity information of the first Doppler signal; determining a first weight for suppressing flash artifacts of each pixel based on the first motion score and a velocity difference value between the first Doppler signal and the second Doppler signal; generating a first Doppler image of the object by applying the first weight to the second Doppler signal of each pixel; and displaying the first Doppler image of the object.

10 Claims, 21 Drawing Sheets

(51) Int. Cl.
    *G01S 7/52*   (2006.01)
    *A61B 8/08*   (2006.01)
    *A61B 8/00*   (2006.01)

(52) U.S. Cl.
    CPC .......... *A61B 8/5207* (2013.01); *A61B 8/5215* (2013.01); *A61B 8/5276* (2013.01); *G01S 7/52074* (2013.01); *G01S 7/52077* (2013.01); *G01S 7/52079* (2013.01); *G01S 7/52084* (2013.01); *G01S 15/899* (2013.01); *A61B 8/4405* (2013.01); *A61B 8/4427* (2013.01); *A61B 8/4472* (2013.01); *A61B 8/467* (2013.01)

(56) References Cited

U.S. PATENT DOCUMENTS

| | | | |
|---|---|---|---|
| 8,758,250 B2 | 6/2014 | Park et al. | |
| 8,992,429 B2 | 3/2015 | Sato | |
| 10,034,638 B2* | 7/2018 | Ansari | A61B 8/5223 |
| 2002/0091319 A1* | 7/2002 | Moehring | G01S 7/52046 |
| | | | 600/454 |
| 2005/0033174 A1* | 2/2005 | Moehring | G01S 7/52071 |
| | | | 600/453 |
| 2006/0064018 A1* | 3/2006 | Chomas | A61B 8/481 |
| | | | 600/459 |
| 2006/0079782 A1* | 4/2006 | Beach | G01S 7/52026 |
| | | | 600/450 |
| 2009/0067699 A1* | 3/2009 | Clark | A61B 8/463 |
| | | | 382/131 |
| 2011/0301470 A1 | 12/2011 | Sato et al. | |
| 2012/0033868 A1* | 2/2012 | Ren | A61B 6/025 |
| | | | 378/21 |
| 2012/0078107 A1* | 3/2012 | Ma | A61B 8/06 |
| | | | 600/454 |
| 2013/0336560 A1* | 12/2013 | Wong | A61B 8/5207 |
| | | | 382/131 |
| 2014/0155752 A1 | 6/2014 | Hwang et al. | |
| 2014/0357999 A1 | 12/2014 | Martins | |
| 2015/0282787 A1 | 10/2015 | Sato | |
| 2016/0058425 A1* | 3/2016 | Wong | A61B 8/5276 |
| | | | 600/453 |
| 2020/0196971 A1* | 6/2020 | Laviola | A61B 6/0414 |

FOREIGN PATENT DOCUMENTS

| | | |
|---|---|---|
| KR | 10-0352639 B1 | 9/2002 |
| KR | 10-1029407 B1 | 4/2011 |

\* cited by examiner

FIG. 9A

| Flash Degree (910) | Motion Score (920) | Weight (930) | | |
| --- | --- | --- | --- | --- |
| | | Low CDD (=0.01) (931) | Middle CDD (=0.5) (932) | High CDD (=0.8) (933) |
| Weak (911) | 0.94 | 0.013 | 0.521 | 0.810 |
| Medium (912) | 2.36 | 1.9e-05 | 0.194 | 0.590 |
| Strong (913) | 4.35 | 2.0e-09 | 0.049 | 0.378 |

FIG. 9B

| Flash Degree (910) | Motion Score (920) | Weight (930) | | |
|---|---|---|---|---|
| | | Low CDD (=0.01) (931) | Middle CDD (=0.5) (932) | High CDD (=0.8) (933) |
| Weak (911) | 0.94 | 0.013 | 0.521 | 1 |
| Medium (912) | 2.36 | 1.9e−05 | 0.194 | 1 |
| Strong (913) | 4.35 | 2.0e−09 | 0.049 | 1 |

FIG. 15

| Flash Degree (1510) | Motion Score (1520) | Weight (1530) x alpha (1540) (Alpha = 1/suppression degree × 100) | | | | | |
|---|---|---|---|---|---|---|---|
| | | Low CDD (=0.01) (1531) | | Middle CDD (=0.5) (1532) | | High CDD (=0.8) (1533) | |
| | | Alpha:1 (suppression degree: 100%) (1541) | Alpha:2 (suppression degree: 50%) (1542) | Alpha:1 (suppression degree: 100%) (1541) | Alpha:2 (suppression degree: 50%) (1542) | Alpha:1 (suppression degree: 100%) (1541) | Alpha:2 (suppression degree: 50%) (1542) |
| Weak (1511) | 0.94 | 0.013 | 0.026 | 0.521 | 1 | 0.810 | 1 |
| Medium (1512) | 2.36 | 1.9e-05 | 3.8e-05 | 0.194 | 0.388 | 0.590 | 1 |
| Strong (1513) | 4.35 | 2.0e-09 | 4.0e-09 | 0.049 | 0.098 | 0.378 | 0.189 |

METHOD OF DISPLAYING DOPPLER IMAGE AND ULTRASOUND DIAGNOSIS APPARATUS FOR PERFORMING THE METHOD

CROSS-REFERENCE TO RELATED APPLICATION

This application is based on and claims priority under 35 U.S.C. § 119 to Korean Patent Application No. 10-2018-0020011, filed on Feb. 20, 2018, in the Korean Intellectual Property Office, the disclosure of which is incorporated by reference herein in its entirety.

BACKGROUND

1. Field

The disclosure relates to a method of displaying a Doppler image and an ultrasound diagnosis apparatus for performing the method.

2. Description of the Related Art

Ultrasound diagnosis apparatuses transmit ultrasound signals toward a predetermined part in a body and obtain images of a cross-section of soft tissue or blood flow by using information about ultrasound signals reflected from the predetermined part.

Ultrasound diagnosis apparatuses have various advantages including a compact size, low cost, and real-time display. Also, ultrasound diagnosis apparatuses have excellent stability because there is no fear of X-ray exposure, and thus the ultrasound diagnosis apparatuses are widely used together with other image diagnosis apparatuses such as X-ray diagnosis apparatuses, computerized tomography (CT) scanners, magnetic resonance imaging (MRI) apparatuses, or nuclear medicine diagnosis apparatuses.

SUMMARY

An objective of one or more embodiments is to provide information about a degree of flash artifact occurrence along with a Doppler image of an object.

Also, an ultrasound diagnosis apparatus according to an embodiment may determine a degree of flash artifact suppression according to a user's setting, and provide information about a degree of remaining flash artifacts along with a Doppler image so that the user may easily adjust the degree of flash artifact suppression.

Additional aspects will be set forth in part in the description which follows and, in part, will be apparent from the description, or may be learned by practice of the presented embodiments.

In accordance with an aspect of the disclosure, a method of displaying a Doppler image includes: obtaining a first Doppler signal where clutter filtering corresponding to each of a plurality of pixels is not performed and a second Doppler signal where clutter filtering corresponding to each of the plurality of pixels is performed; determining a first motion score indicating a degree of flash artifact occurrence by using velocity information of the first Doppler signal; generating a Doppler image of an object by using at least one of the first Doppler signal and the second Doppler signal; and displaying the Doppler image.

The generating of the Doppler image may include: determining a first weight for suppressing flash artifacts of each pixel based on the first motion score and a velocity difference value between the first Doppler signal and the second Doppler signal; and generating a first Doppler image of the object by applying the first weight to the second Doppler signal of each pixel, and the displaying of the Doppler image may include displaying the first Doppler image along with the first motion score.

The generating of the Doppler image may include generating a second Doppler image of the object by using the second Doppler signal, and the displaying of the Doppler image may include displaying the second Doppler image along with the first motion score.

The velocity information of the first Doppler signal may include a mean velocity of the first Doppler signal and a velocity standard deviation of the first Doppler signal.

The determining of the first motion score may include determining the first motion score by using velocity distribution information of the first Doppler signal having a power greater than a mean power.

The generating of the Doppler image of the object may include: receiving an input that sets a flash artifact degree of flash artifact suppression from a user; determining a second weight corresponding to the set degree of flash artifact suppression; and generating a third Doppler image of the object by applying the first weight and the second weight to the second Doppler signal of each pixel.

The method may further include providing information indicating the degree of flash artifact suppression.

The providing of the information indicating the degree of flash artifact suppression may include displaying, along with the first motion score, a second motion score indicating a degree of remaining flash artifacts after the first weight and the second weight are applied.

The determining of the first weight may include determining the first weight to decrease as the velocity difference value between the first Doppler signal and the second Doppler signal decreases.

The determining of the first weight may include determining the first weight to decrease as the first motion score increases.

The determining of the first weight may include: determining first pixels for which a velocity value of the first Doppler signal is greater than a threshold value as outliers; determining pixels other than the first pixels from among the plurality of pixels as second pixels for suppressing the flash artifacts; and determining the first weight corresponding to each of the second pixels based on the first motion score and the velocity difference value between the first Doppler signal and the second Doppler signal.

The determining of the first weight may include determining that the first weight is 1 when the velocity difference value between the first Doppler signal and the second Doppler signal is greater than a threshold value.

In accordance with another aspect of the disclosure, an ultrasound diagnosis apparatus includes: a controller configured to obtain a first Doppler signal where clutter filtering corresponding to each of a plurality of pixels is not performed and a second Doppler signal where clutter filtering corresponding to each of the plurality of pixels is performed, and determine a first motion score indicating a degree of flash artifact occurrence by using velocity information of the first Doppler signal; an image processor configured to generate a Doppler image of an object by using at least one of the first Doppler signal and the second Doppler signal; and a display for displaying the Doppler image and the first motion score.

In accordance with another aspect of the disclosure, a computer program product includes a computer-readable storage medium, wherein the computer-readable storage medium includes instructions, when executed on a computing device, causing the computing device to: obtain a first Doppler signal where clutter filtering corresponding to each of a plurality of pixels is not performed and a second Doppler signal where clutter filtering corresponding to each of the plurality of pixels is performed; determine a first motion score indicating a degree of flash artifact occurrence by using velocity information of the first Doppler signal; generate a Doppler image of an object by using at least one of the first Doppler signal and the second Doppler signal; and display the Doppler image along with the first motion score.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 9A and 9B are tables for determining a weight for suppressing flash artifacts of each pixel, according to an embodiment;

FIG. 15 is a table for determining a weight for suppressing flash artifacts of each pixel based on an input that sets a degree of flash artifact suppression, according to an embodiment;

DETAILED DESCRIPTION

Figure 1:
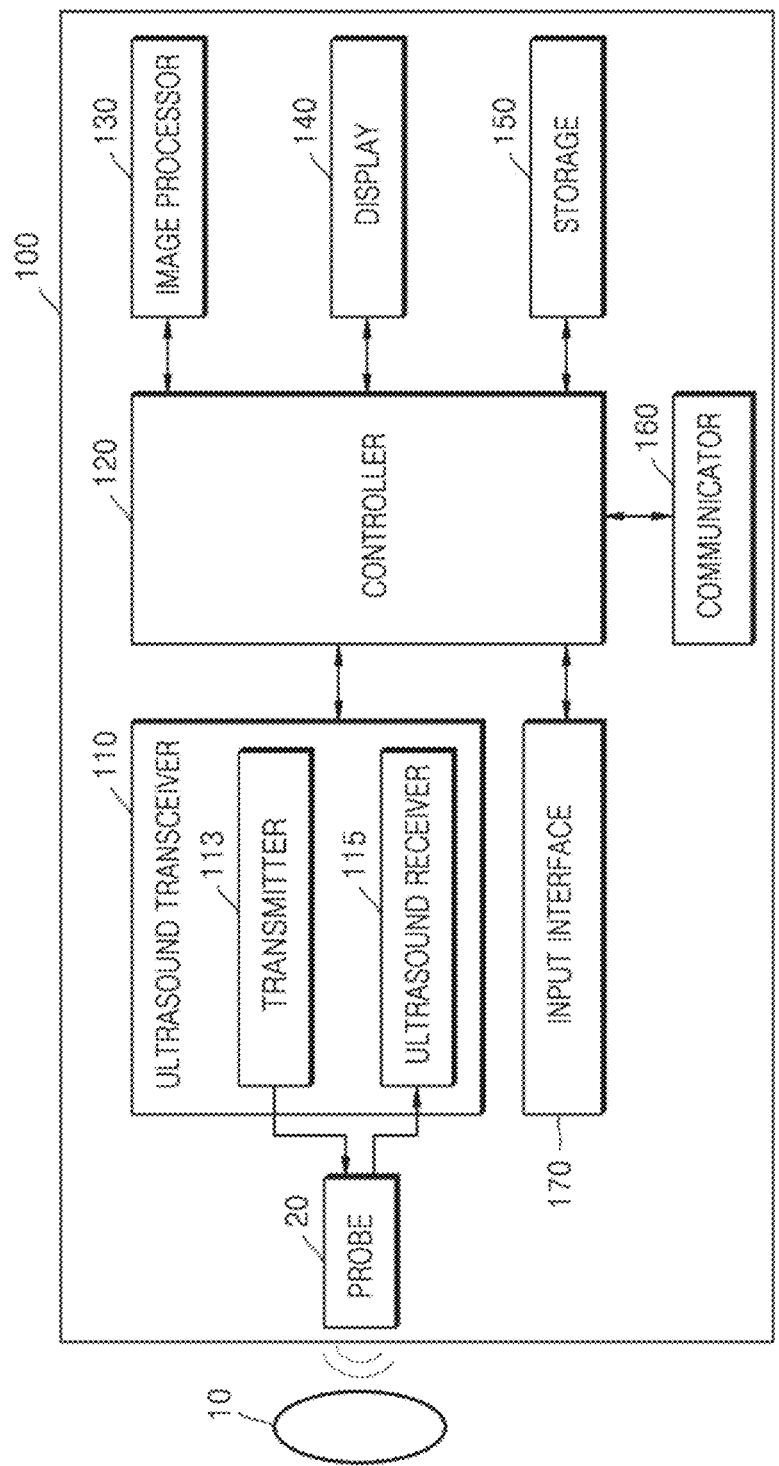
FIG. 1 is a block diagram illustrating a configuration of an ultrasound diagnosis apparatus according to an embodiment.

The principle of the present disclosure is explained and embodiments are disclosed so that the scope of the present disclosure is clarified and one of ordinary skill in the art to which the present disclosure pertains implements the present disclosure. The disclosed embodiments may have various forms.

Throughout the specification, like reference numerals or characters refer to like elements. In the present specification, all elements of embodiments are not explained, but general matters in the technical field of the present disclosure or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the present disclosure and embodiments thereof will now be described more fully with reference to the accompanying drawings.

In the present specification, an image may include a medical image obtained by a medical imaging apparatus such as a magnetic resonance imaging (MRI) apparatus, a computed tomography (CT) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

Throughout the specification, the term "ultrasound image" refers to an image of an object processed based on ultrasound signals transmitted to the object and reflected therefrom.

Throughout the specification, the term "Doppler image" refers to an image obtained by receiving information about a velocity or a movement direction of a moving object (e.g., blood flow) by using a change in a frequency of reflected sound waves due to the Doppler effect and converting the information into an image. Examples of the Doppler image may include, but are not limited to, an image showing power of blood flow by measuring an intensity of a reflected ultrasound echo signal and an image showing both power and a direction of blood flow.

As used herein, the term "and/or" includes any and all combinations of one or more of the associated listed items. Expressions such as "at least one of", when preceding a list of elements, modify the entire list of elements and do not modify the individual elements of the list.

Embodiments will now be described in detail with reference to the drawings.

FIG. 1 is a block diagram illustrating a configuration of an ultrasound diagnosis apparatus 100 according to an embodiment.

The ultrasound diagnosis apparatus 100 according to an embodiment may include a probe 20, an ultrasound transceiver 110, a controller 120, an image processor 130, a display 140, a storage 150, a communicator 160, and an input interface 170.

The ultrasound diagnosis apparatus 100 may be a cart-type or portable-type ultrasound diagnosis apparatus. Examples of the portable-type ultrasound diagnosis apparatus may include, but are not limited to, a smartphone, a laptop computer, a personal digital assistant (PDA), and a tablet personal computer (PC).

The probe 20 may include a plurality of transducers. The plurality of transducers may transmit ultrasound signals to an object 10 in response to transmitting signals applied from a transmitter 113. The plurality of transducers may receive ultrasound signals reflected from the object 10 to generate reception signals. In addition, the probe 20 and the ultrasound diagnosis apparatus 100 may be formed in one body, or the probe 20 and the ultrasound diagnosis apparatus 100 may be formed separately but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analogue to digital signals and summing the reception signals converted into digital form, based on a position and a focal point of the plurality of transducers.

The controller 120 according to an embodiment may obtain a first Doppler signal where clutter filtering corresponding to each of a plurality of pixels is not performed and a second Doppler signal where clutter filtering corresponding to each of the plurality of pixels is performed.

The controller 120 may determine a first motion score indicating a degree of flash artifact occurrence by using velocity information of the first Doppler signal. For example, the controller 120 may determine the first motion score by using a velocity and a velocity standard deviation of the first Doppler signal having a power greater than a mean power.

The controller 120 may determine a first weight for suppressing flash artifacts of each pixel based on the first motion score and a velocity difference value between the first Doppler signal and the second Doppler signal. For example, the controller 120 may determine the first weight to decrease as the velocity difference value between the first Doppler signal and the second Doppler signal decreases. The controller 120 may determine the first weight to decrease as the first motion score increases. The controller 120 may determine that the first weight is 1, when the velocity difference value between the first Doppler signal and the second Doppler signal is greater than a threshold value.

According to an embodiment, the controller 120 may receive an input that sets a degree of flash artifact suppression from a user through the input interface 170. The controller 120 may determine a second weight corresponding to the set degree of flash artifact suppression. The controller 120 may generate a Doppler image of an object by applying the first weight and the second weight to the second Doppler signal of each pixel.

The controller 120 may determine first pixels for which a velocity value of the first Doppler signal is greater than a threshold value as outliers. The controller 120 may determine pixels other than the first pixels from among the plurality of pixels as second pixels for suppressing flash artifacts. The controller 120 may determine the first weight corresponding to each of the second pixels based on the first motion score and the velocity difference value between the first Doppler signal and the second Doppler signal. In this case, the threshold value for determining outliers may be determined based on the first motion score.

The image processor 130 may generate an ultrasound image by using the ultrasound data generated by the ultrasound receiver 115.

According to an embodiment, the image processor 130 may generate the Doppler image by using at least one of the first Doppler signal where clutter filtering is not performed and the second Doppler signal where clutter filtering is performed. For example, the image processor 130 may generate a first Doppler image of the object from which flash artifacts are suppressed by applying the first weight to the second Doppler signal of each pixel. The image processor 130 may generate a third Doppler image of the object by further applying a second weight to the second Doppler signal of each pixel.

According to an embodiment, the image processor 130 may generate a second Doppler image from which flash artifacts are not suppressed. For example, the image processor 130 may generate the second Doppler image from which flash artifacts are not suppressed by using only the first Doppler signal where clutter filtering of each pixel is not performed. Alternatively, the image processor 130 may generate the second Doppler image from which flash artifacts are not suppressed by using only the second Doppler signal where clutter filtering of each pixel is performed.

The display 140 may display the generated ultrasound image and various pieces of information processed by the ultrasound diagnosis apparatus 100. The ultrasound diagnosis apparatus 100 may include one or more displays 140 according to embodiments. Also, the display 140 may include a touchscreen in combination with a touch panel.

The display 140 may display the Doppler image and the first motion score. The display 140 may provide information indicating a degree of flash artifact suppression. For example, the display 140 may provide the information indicating the degree of flash artifact suppression by displaying a second motion score indicating a degree of remaining flash artifacts after the first weight and the second weight are applied, along with the first motion score.

The controller 120 may control operations of the ultrasound diagnosis apparatus 100 and the flow of signals between internal elements of the ultrasound diagnosis apparatus 100. The controller 120 may include a memory for storing a program or data for performing functions of the ultrasound diagnosis apparatus 100 and a processor for processing the program or data. Also, the controller 120 may control an operation of the ultrasound diagnosis apparatus 100 by receiving a control signal from the input interface 170 or an external apparatus.

The ultrasound diagnosis apparatus 100 may include the communicator 160, and may be connected to external apparatuses (e.g., a server, a medical apparatus, and a table device (e.g., a smartphone, a tablet personal computer (PC), or a wearable device)) via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

Alternatively, the controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of an operation of the controller 120 or the entire operation of the controller 120.

The program may be pre-installed in the external apparatus or may be installed by a user of the external apparatus by downloading the program from a server that provides applications. The server that provides the applications may include a recording medium where the program is stored.

The storage 150 may store various data or programs for driving and controlling the ultrasound diagnosis apparatus 100, input/output ultrasound data, and the obtained ultrasound image.

The input interface 170 may receive the user's input for controlling the ultrasound diagnosis apparatus 100. Examples of the user's input may include, but are not limited to, inputs for manipulating buttons, keypads, mice, trackballs, jog switches, or knobs, inputs for touching a touchpad or a touchscreen, a voice input, a motion input, and a bioinformation input (e.g., iris recognition or fingerprint recognition).

Examples of the input interface 170 may include, but are not limited to, a sub-display that is implemented as a touchscreen in a cart-type ultrasound diagnosis apparatus, a control panel including a hardware button, and a touchscreen of a portable-type ultrasound diagnosis apparatus.

An example of the ultrasound diagnosis apparatus 100 according to an embodiment will now be described with reference to FIGS. 2A, 2B, and 2C.

Figure 2C:
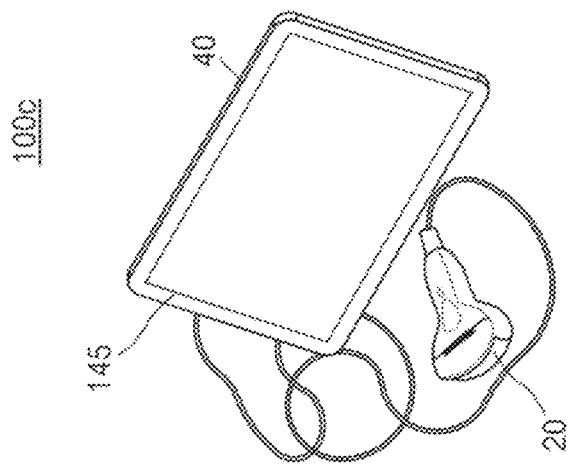
FIGS. 2A through 2C are views illustrating ultrasound diagnosis apparatuses according to an embodiment.
Figure 2B:
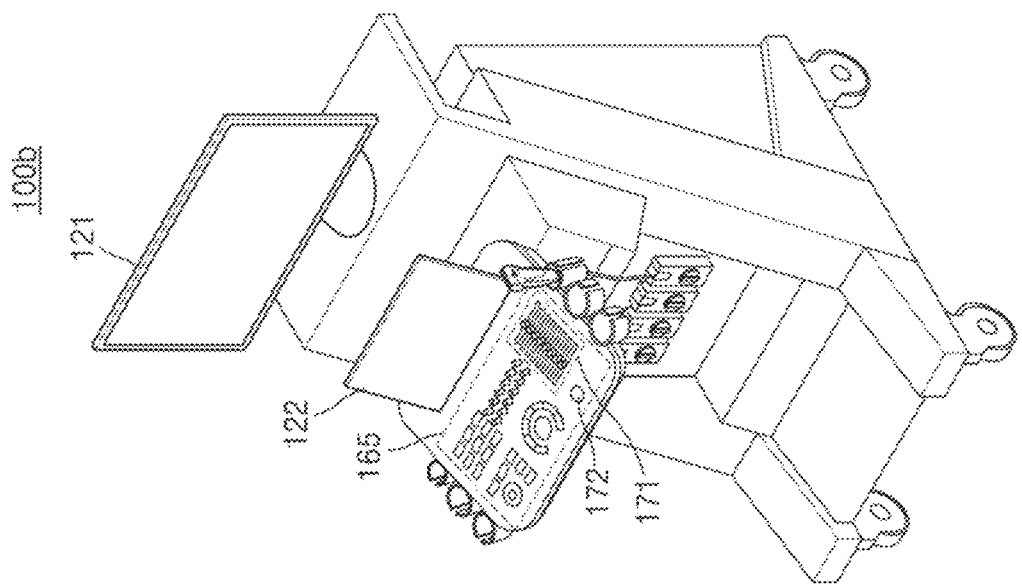
Figure 2A:
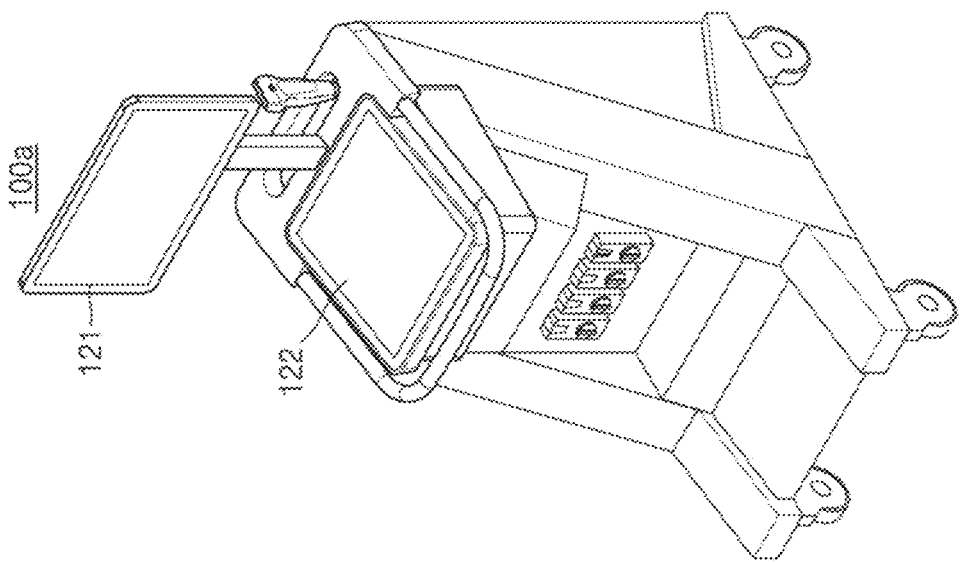

FIGS. 2A, 2B, and 2C are views illustrating ultrasound diagnosis apparatuses 100a, 100b, and 100c according to an embodiment.

Referring to FIGS. 2A and 2B, each of the ultrasound diagnosis apparatuses 100a and 100c may include a main display 121 and a sub-display 122. At least one among the main display 121 and the sub-display 122 may be a touchscreen. The main display 121 and the sub-display 122 may display ultrasound images and/or various information processed by the ultrasound diagnosis apparatuses 100a and 100b. According to an embodiment, the main display 121 may display an ultrasound image and the sub-display 122 may display a control panel for controlling display of the ultrasound image as a graphical user interface (GUI). The sub-display 122 may receive control data for controlling display of an image through the control panel displayed as the GUI. The ultrasound diagnosis apparatuses 100a and 100b may control the display of the ultrasound image on the main display 121 by using the received control data.

Referring to FIG. 2B, the ultrasound diagnosis apparatus 100b may further include a control panel 165 in addition to the main display 121 and the sub-display 122. The control panel 165 may include buttons, trackballs, jog switches, or knobs, and may receive data for controlling the ultrasound diagnosis apparatus 100b from a user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, or knobs included in the control panel 165 may be provided as a GUI on the main display 121 or the sub-display 122.

Referring to FIG. 2C, the ultrasound diagnosis apparatus 100c may be a portable-type ultrasound diagnosis apparatus. Examples of the portable-type ultrasound diagnosis apparatus 100c may include, but are not limited to, a smartphone including a probe and an application, a laptop computer, a PDA, and a tablet PC.

The ultrasound diagnosis apparatus 100c may include the probe 20 and a main body 40. The probe 20 may be connected to one side of the main body 40 by wire or wirelessly. The main body 40 may include a touchscreen 145. The touchscreen 145 may display an ultrasound image, various pieces of information processed by the ultrasound diagnosis apparatus 100c, and a GUI.

Figure 3:
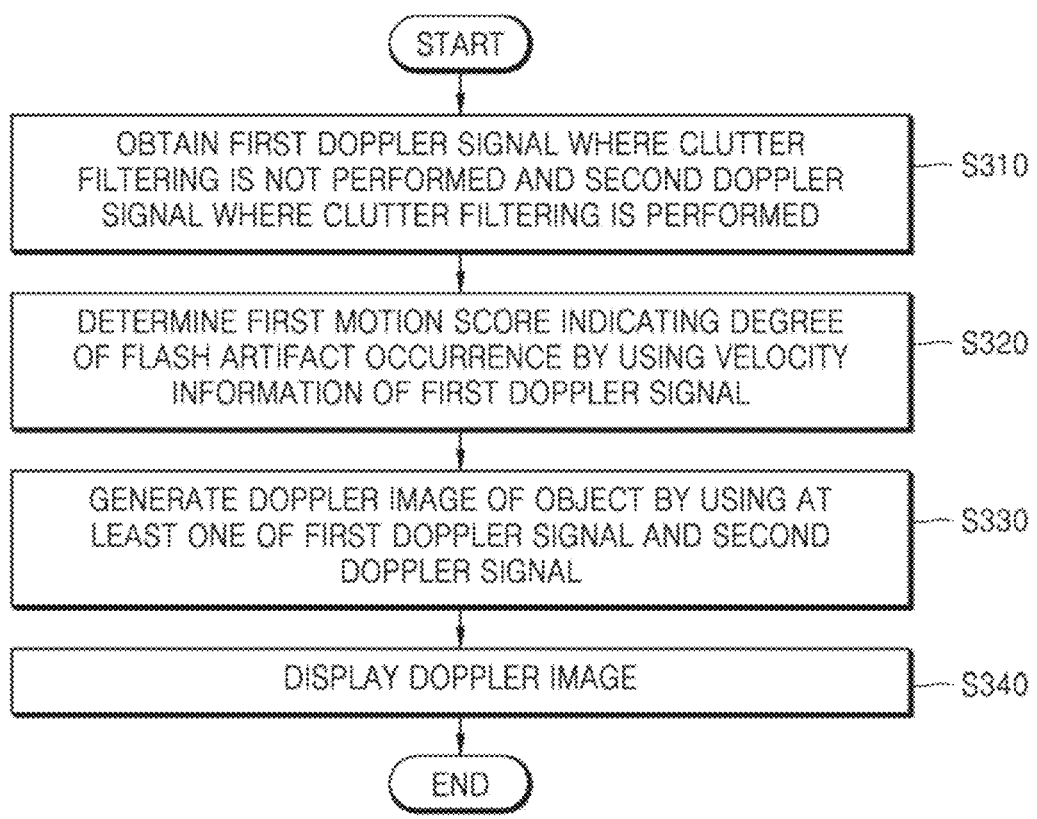
FIG. 3 is a flowchart of a method of displaying a Doppler image according to an embodiment.

FIG. 3 is a flowchart of a method of displaying a Doppler image according to an embodiment.

In operation S310, the ultrasound diagnosis apparatus 100 may obtain a first Doppler signal where clutter filtering is not performed and a second Doppler signal where clutter filtering is performed. According to an embodiment, the ultrasound diagnosis apparatus 100 may obtain the first Doppler signal and the second Doppler signal corresponding to each of a plurality of pixels.

Figure 4:
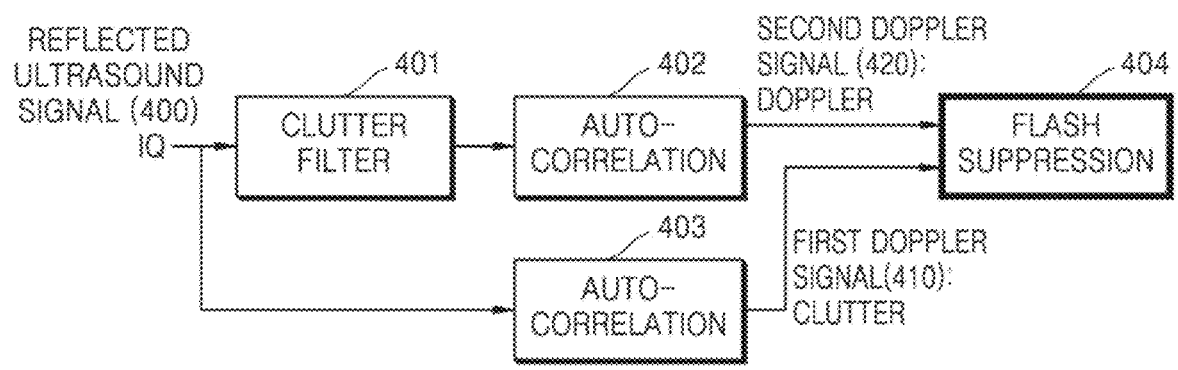
FIG. 4 is a block diagram for explaining a first Doppler signal where clutter filtering is not performed and a second Doppler signal where clutter filtering is performed.

For example, referring to FIG. 4, the ultrasound diagnosis apparatus 100 may generate a first Doppler signal 410 where clutter filtering is not performed by applying an auto-correlation function 403 to a reflected ultrasound signal 400. Also, the ultrasound diagnosis apparatus 100 may perform clutter filtering on the reflected ultrasound signal 400 by using a clutter filter 401, and may generate a second Doppler signal 420 by applying an auto-correlation function 402 to the clutter filtered ultrasound signal.

Clutter filtering may refer to a process of obtaining a pure blood flow Doppler signal by removing an undesirable noise signal (e.g., a signal generated due to a strong movement of a probe or a movement of tissue) by filtering a reflected ultrasound signal. For example, not only a signal reflected from red cells of a blood vessel but also a signal reflected from muscular tissue such as a blood vessel wall exist in a reflected ultrasound signal, thereby leading to an error in calculating an actual blood flow velocity. In general, a signal reflected from a stopped matter or a slowly moving matter such as tissue or muscle is stronger by about 40 db to about 100 db than a signal reflected from red cells in blood. A signal reflected from rapidly moving blood cells has a larger Doppler frequency shift than a signal reflected from slowly moving tissue. Hence, when a low-frequency signal reflected from slowly moving tissue is removed from a reflected ultrasound signal by using an appropriate high-pass filter, an ultrasound Doppler signal reflected from red cells may be obtained. As such, a filter used to obtain a desirable ultrasound Doppler image from a distorted ultrasound echo signal is referred to as a clutter filter.

According to an embodiment, examples of the clutter filter may include, but are not limited to, a finite impulse response (FIR) filter, an FIR filter with a linear phase, an FIR filter with a minimum phase, an infinite impulse response (IIR) filter, a regression filter, and an adaptive filter.

However, flash artifacts may not be completely suppressed even after clutter filtering is performed on a reflected ultrasound signal by using a clutter filter. Flash artifacts refer to artifacts with a very low blood flow velocity or a very high blood flow power in a Doppler image due to a movement of the probe 20 or a movement of human tissue when a Doppler image is obtained. Hereinafter, flash artifacts may be referred to as a flash for convenience of explanation.

Accordingly, the ultrasound diagnosis apparatus 100 needs to suppress (404) flash artifacts included in the second Doppler signal 420 where clutter filtering is performed in order to obtain a high-quality Doppler image. Hereinafter, for convenience of explanation, the first Doppler signal 410 where clutter filtering is not performed may be referred to as a clutter signal, and the second Doppler signal 420 where clutter filtering is performed may be referred to as a Doppler signal.

Referring back to FIG. 3, in operation S320, the ultrasound diagnosis apparatus 100 may determine a first motion score indicating a degree of flash artifact occurrence by using velocity information of the first Doppler signal 410. The velocity information may include, but is not limited to, a mean velocity of the first Doppler signal 410 where clutter filtering is not performed and a velocity standard deviation of the first Doppler signal 410.

According to an embodiment, the ultrasound diagnosis apparatus 100 may estimate the first motion score by using the mean velocity of the first Doppler signal 410 and the velocity standard deviation of the first Doppler signal 410. According to an embodiment, the ultrasound diagnosis apparatus 100 may determine the first motion score by using velocity distribution information (e.g., the mean velocity and the velocity standard deviation) of the first Doppler signal 410 having a power greater than a mean power.

For example, the ultrasound diagnosis apparatus 100 may determine the first motion score by using Equation 1.

$$\text{Motion Score} = C_1 * m_{vel_C} + C_2 * \sigma_{vel_C}$$

$$m_{vel_C} = \text{mean}(|\text{Clutter}_{velocity}|[\text{Clutter}_{power,dB} > m_{Clutter_{power,db}}])$$

$$\sigma_{vel_C} = \text{std}(|\text{Clutter}_{velocity}|[\text{Clutter}_{power,dB} > m_{Clutter_{power,db}}]) \quad (1)$$

where '$m_{vel_C}$' refers to the mean velocity of the first Doppler signal $|\text{Clutter}_{velocity}|[\text{Clutter}_{power,db} > m_{Clutter_{power,db}}]$ having the power greater than the mean power, and '$\sigma_{vel_C}$' refers to the velocity standard deviation of the first Doppler signal $|\text{Clutter}_{velocity}|[\text{Clutter}_{power,db} > m_{Clutter_{power,db}}]$ having the power greater than the mean power. $C_1$ and $C_2$ that are constant values may be defined in any of various ways. For example, when the constant value $C_1$ is '1' and the constant value $C_2$ is '2', the first motion score may be calculated as '$m_{vel_C} + 2\sigma_{vel_C}$'.

The first motion score may be calculated by applying a log to Equation 1 or adding a constant value $C_3$ to Equation 1. For example, the ultrasound diagnosis apparatus 100 may determine the first motion score by using Equation 2.

$$\text{Motion Score} = \ln(C_1 * m_{vel_C} + C_2 * \sigma_{vel_C} + C_3) \quad (2)$$

Since the first motion score indicates the degree of flash artifact occurrence, the first motion score may increase as the degree of flash artifact occurrence increases. For convenience of explanation, a case where the degree of flash artifact occurrence is less than a first threshold value is defined as a weak flash, a case where the degree of flash artifact occurrence is between the first threshold value and a second threshold value is defined as a medium flash, and a case where the degree of flash artifact occurrence is greater than the second threshold value is defined as a strong flash. The first motion score will be described below in detail with reference to FIG. 7.

In operation S330, the ultrasound diagnosis apparatus 100 may generate a Doppler image of an object by using at least one of the first Doppler signal 410 and the second Doppler signal 420.

Examples of the Doppler image may include, but are not limited to, a color Doppler image that represents a velocity of a moving object in a color by using the Doppler effect, a spectral Doppler image that represents an image of a moving object in a spectrum by using the Doppler effect, and a power Doppler image that represents the number of structures (e.g., red cells in blood) or an intensity of a Doppler signal in a color.

According to an embodiment, the ultrasound diagnosis apparatus 100 may generate a first Doppler image from which flash artifacts are suppressed by using the first Doppler signal 410 and the second Doppler signal 420. For example, the ultrasound diagnosis apparatus 100 may determine a first weight for suppressing flash artifacts of each pixel, and may generate the first Doppler image from which flash artifacts are suppressed by applying the first weight to the second Doppler signal 420 of each pixel. An operation by which the ultrasound diagnosis apparatus 100 generates the first Doppler image from which flash artifacts are suppressed will now be described in detail.

According to an embodiment, the ultrasound diagnosis apparatus 100 may determine the first weight for suppressing flash artifacts of each pixel based on the first motion score and a velocity difference value between the first Doppler signal 410 and the second Doppler signal 420. The first weight may be a value between, but not limited to, 0 and 1.

According to an embodiment, the ultrasound diagnosis apparatus 100 may determine the velocity difference value between the first Doppler signal 410 where clutter filtering of each pixel is not performed and the second Doppler signal 420 where clutter filtering is performed. The ultrasound diagnosis apparatus 100 may determine the first weight of each pixel to decrease as the velocity difference value between the first Doppler signal 410 and the second Doppler signal 420 decreases. For example, when the velocity difference value between the first Doppler signal 410 and the second Doppler signal 420 of a first pixel is '0.1' and the velocity difference value between the first Doppler signal 410 and the second Doppler signal 420 of a second pixel is '0.8', the first weight of the first pixel may be determined to be less than the first weight of the second pixel. A pixel for which the velocity difference value between the first Doppler signal 410 and the second Doppler signal 420 is small is likely to have flash artifacts. Accordingly, the ultrasound diagnosis apparatus 100 may cause the pixel to be hardly displayed on the Doppler image by applying a small weight to the pixel for which the velocity difference value between the first Doppler signal 410 and the second Doppler signal 420 is small.

According to an embodiment, the ultrasound diagnosis apparatus 100 may determine the first weight by using the first motion score instead of the velocity difference value between the first Doppler signal 410 and the second Doppler signal 420. For example, the ultrasound diagnosis apparatus 100 may determine the first weight to decrease as the first motion score increases, and may determine the first weight to increase as the first motion score decreases. When the first motion score increases, it means that the degree of flash artifact occurrence increases. Accordingly, the ultrasound diagnosis apparatus 100 may determine a smaller weight for a corresponding pixel to suppress strong flash artifacts.

According to an embodiment, when the velocity difference value between the first Doppler signal 410 and the second Doppler signal 420 is greater than a threshold value, the ultrasound diagnosis apparatus 100 may determine that the first weight is 1. For example, when the velocity difference value between the first Doppler signal 410 and the second Doppler signal 420 is greater than the threshold value, the ultrasound diagnosis apparatus 100 may determine a corresponding pixel as a blood flow pixel irrespective of the first motion score, and may determine that the first weight of the corresponding pixel is '1'.

The velocity difference value between the first Doppler signal 410 and the second Doppler signal 420 may be expressed by using a clutter to Doppler velocity difference (CDD) for convenience of explanation.

According to an embodiment, the ultrasound diagnosis apparatus 100 may determine first pixels for which a velocity value of the first Doppler signal 410 is greater than a threshold value as outliers, and may determine pixels other than the first pixels from among the plurality of pixels as second pixels for suppressing flash artifacts. The ultrasound diagnosis apparatus 100 may determine the first weight corresponding to each of the second pixels based on the first motion score and the velocity difference value between the first Doppler signal 410 and the second Doppler signal 420. For example, the ultrasound diagnosis apparatus 100 may determine the first pixels for which the velocity value of the first Doppler signal 410 is greater than the threshold value as outliers, and may not apply an algorithm for suppressing flash artifacts to the outliers, in order to prevent a blood flow pixel having a low CDD from being removed. An operation by which the ultrasound diagnosis apparatus 100 determines outliers will be described below in detail with reference to FIG. 10.

According to an embodiment, the ultrasound diagnosis apparatus 100 may generate a first Doppler image of the object by applying the first weight to the second Doppler signal 420 of each pixel. Since the first weight may be determined to be close to '1' for a blood flow component (referred to as blood for convenience of explanation) and may be determined to be close to '0' for a component including flash artifacts (referred to as a clutter for convenience of explanation), a high-quality blood flow Doppler image may be generated when the ultrasound diagnosis apparatus 100 applies the first weight to the second Doppler signal 420 of each pixel.

According to an embodiment, the ultrasound diagnosis apparatus 100 may generate a second Doppler image from which flash artifacts are not suppressed. For example, the ultrasound diagnosis apparatus 100 may generate the second Doppler image from which flash artifacts are not suppressed by using only the first Doppler signal 410 where clutter filtering of each pixel is not performed. Alternatively, the ultrasound diagnosis apparatus 100 may generate the second Doppler image from which flash artifacts are not suppressed by using only the second Doppler signal 420 where clutter filtering of each pixel is performed.

In operation S340, the ultrasound diagnosis apparatus 100 may display the Doppler image.

According to an embodiment, the ultrasound diagnosis apparatus 100 may display the first Doppler image from which flash artifacts are suppressed along with the first motion score. According to another embodiment, the ultrasound diagnosis apparatus 100 may display the second Doppler image from which flash artifacts are not suppressed along with the first motion score. The first motion score may be displayed in any of various forms. According to an embodiment, the ultrasound diagnosis apparatus 100 may display the first motion score as a value or in the form of a graph. For example, the ultrasound diagnosis apparatus 100 may represent the first motion score in the form of a bar or a circular shape. The ultrasound diagnosis apparatus 100 may display the first motion score in a specific color.

According to an embodiment, the ultrasound diagnosis apparatus 100 may display the first motion score over the Doppler image. Alternatively, the ultrasound diagnosis apparatus 100 may display the first motion score so that the first motion score does not overlap the Doppler image.

According to an embodiment, some of operations S310 through S340 may be omitted or an order of some operations may be changed. For example, operation S330 may be performed earlier than operation S320.

Since the first motion score indicates the degree of flash artifact occurrence, when the ultrasound diagnosis apparatus 100 displays the Doppler image along with flash artifacts, a user may intuitively know the degree of flash artifact occurrence when obtaining the Doppler image. The algorithm for suppressing flash artifacts will now be described with reference to FIG. 5.

Figure 5:
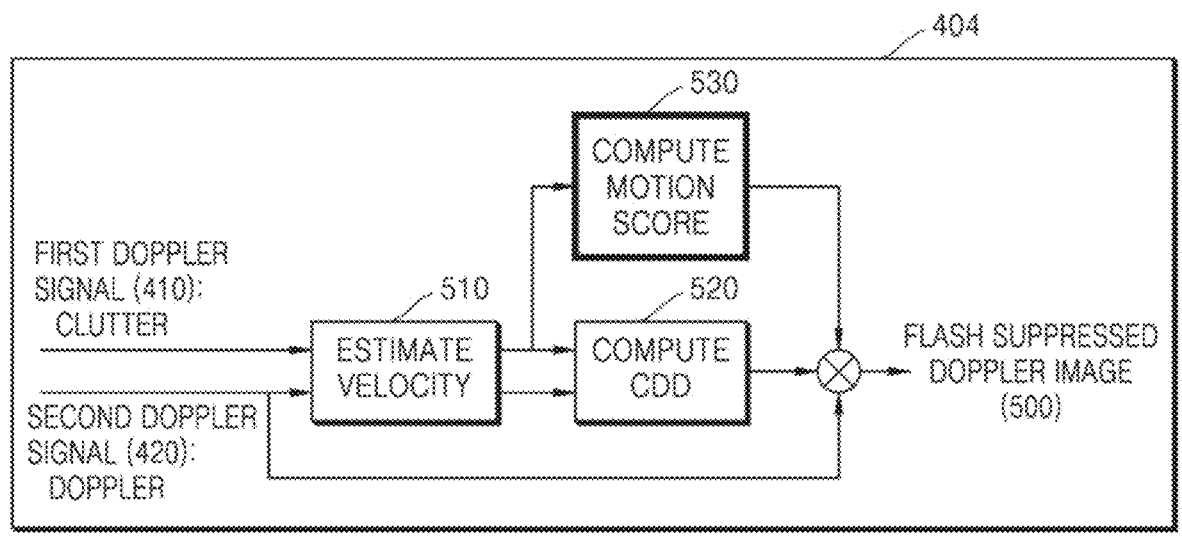
FIG. 5 is a block diagram for explaining an algorithm for suppressing flash artifacts, according to an embodiment.

FIG. 5 is a block diagram for explaining an algorithm for suppressing flash artifacts according to an embodiment.

Referring to FIG. 5, the ultrasound diagnosis apparatus 100 may obtain velocity information from each of the first Doppler signal 410 where clutter filtering is not performed and the second Doppler signal 420 where clutter filtering is performed [510]. For example, the ultrasound diagnosis apparatus 100 may estimate a first velocity from the first Doppler signal 410, and may estimate a second velocity from the second Doppler signal 420. The ultrasound diagnosis apparatus 100 may determine a velocity difference value (e.g., CDD) between the first Doppler signal 410 and the second Doppler signal 420 by using the first velocity and the second velocity [520]. For example, a CDD will now be described with reference to FIG. 6.

Figure 6:
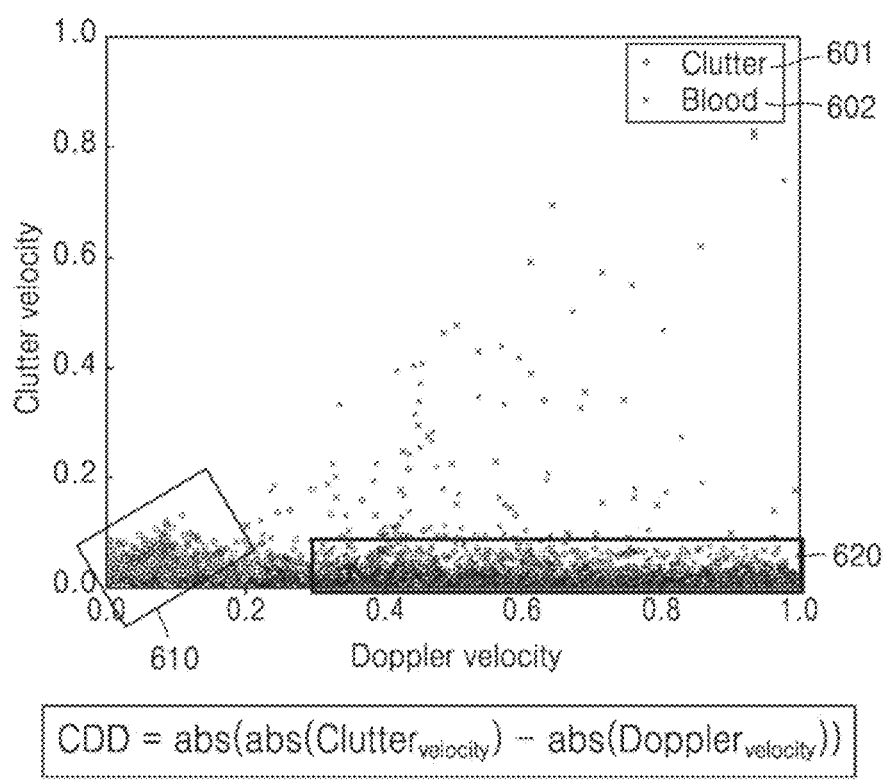
FIG. 6 is a diagram for explaining velocity information of a first Doppler signal and a second Doppler signal.

In FIG. 6, a velocity of the first Doppler signal 410 where clutter filtering is not performed may be referred to as a 'clutter velocity', and a velocity of the second Doppler signal 420 where clutter filtering is performed may be referred to as a 'Doppler velocity'. According to an embodiment, as shown in Equation 3, a CDD may be calculated as an absolute value of a difference between the velocity clutter$_{velocity}$ of the first Doppler signal 410 and the velocity Doppler$_{velocity}$ of the second Doppler signal 420.

$$CDD=abs(abs(clutter_{velocity})-abs(Doppler_{velocity})) \quad (3)$$

Referring to FIG. 6, the CDD may decrease toward a diagonal area and may increase away from the diagonal area. For example, the CDD of a clutter component (a component other than blood flow) 601 gathered in a diagonal area 600 that is a lower left area may be small. In contrast, the CDD of a blood flow component 602 gathered in an area 620 that is a lower right area may be large. Accordingly, when the CDD of a first pixel is small, the first pixel is likely to be the clutter component 601, and thus the ultrasound diagnosis apparatus 100 may determine a first weight of the first pixel to be high. When the CDD of a second pixel is large, the second pixel is likely to be the blood flow component 602, and thus, the ultrasound diagnosis apparatus 100 may determine the first weight of the second pixel to be low.

Referring back to FIG. 5, the ultrasound diagnosis apparatus 100 may determine a first motion score indicating a degree of flash artifact occurrence by using velocity information of the first Doppler signal 410 [530]. According to an embodiment, the ultrasound diagnosis apparatus 100 may determine the first motion score by using velocity distribution information (e.g., a mean velocity and a velocity standard deviation) of the first Doppler signal 410 having a power greater than a mean power.

Figure 7:
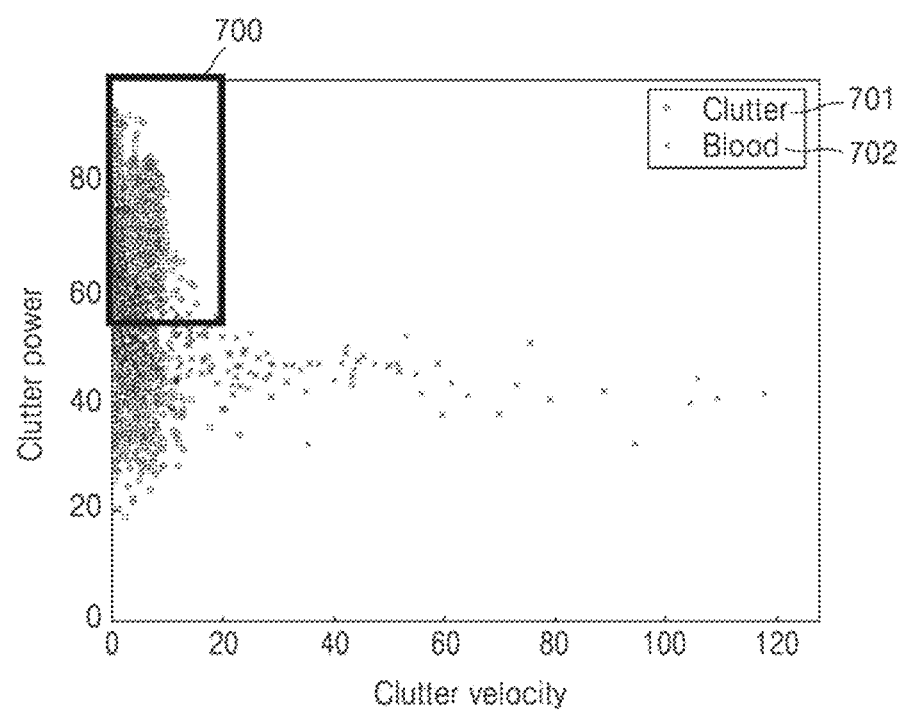
FIG. 7 is a diagram for explaining a motion score according to an embodiment.

For example, referring to FIG. 7, the first motion score may be determined by using Equation 4. In FIG. 7, since the velocity clutter$_{velocity}$ of the first Doppler signal 410 is normalized to have a value ranging from 1 to 128, the ultrasound diagnosis apparatus 100 may determine the first motion score by dividing a sum of a mean velocity $m_{vel_C}$ and a velocity standard deviation $2\sigma_{vel_C}$ by 128 as follows.

$$\text{Motion Score} = (m_{vel_C} + 2\sigma_{vel_C})/128 \quad (4)$$

For example, a mean value of a clutter power of the first Doppler signal 410 is '55', a mean velocity of a clutter component 701 and a blood flow component 702 included in an area 700 having a power greater than 55 is '6', and a standard deviation is '3', the ultrasound diagnosis apparatus 100 may determine that the first motion score is '0.09(=(6+3*2)/128)'. In this case, since the first motion score (0.09) is less than a threshold value (e.g., 0.1), the ultrasound diagnosis apparatus 100 may determine that the degree of flash artifact occurrence is weak.

In contrast, although not shown in FIG. 7, when a mean value of a clutter power of the first Doppler signal 410 is '60', a mean velocity of components having a power greater than 60 is '50', and a standard deviation is '25', the ultrasound diagnosis apparatus 100 may determine that the first motion score is '0.78(=(50+25*2)/128)'. In this case, the first motion score (0.78) is greater than a threshold value (e.g., 0.5), the ultrasound diagnosis apparatus 100 may determine that the degree of flash artifact occurrence is strong. A relationship between flash artifacts and a motion score will now be described in more detail with reference to FIG. 8.

Figure 8:
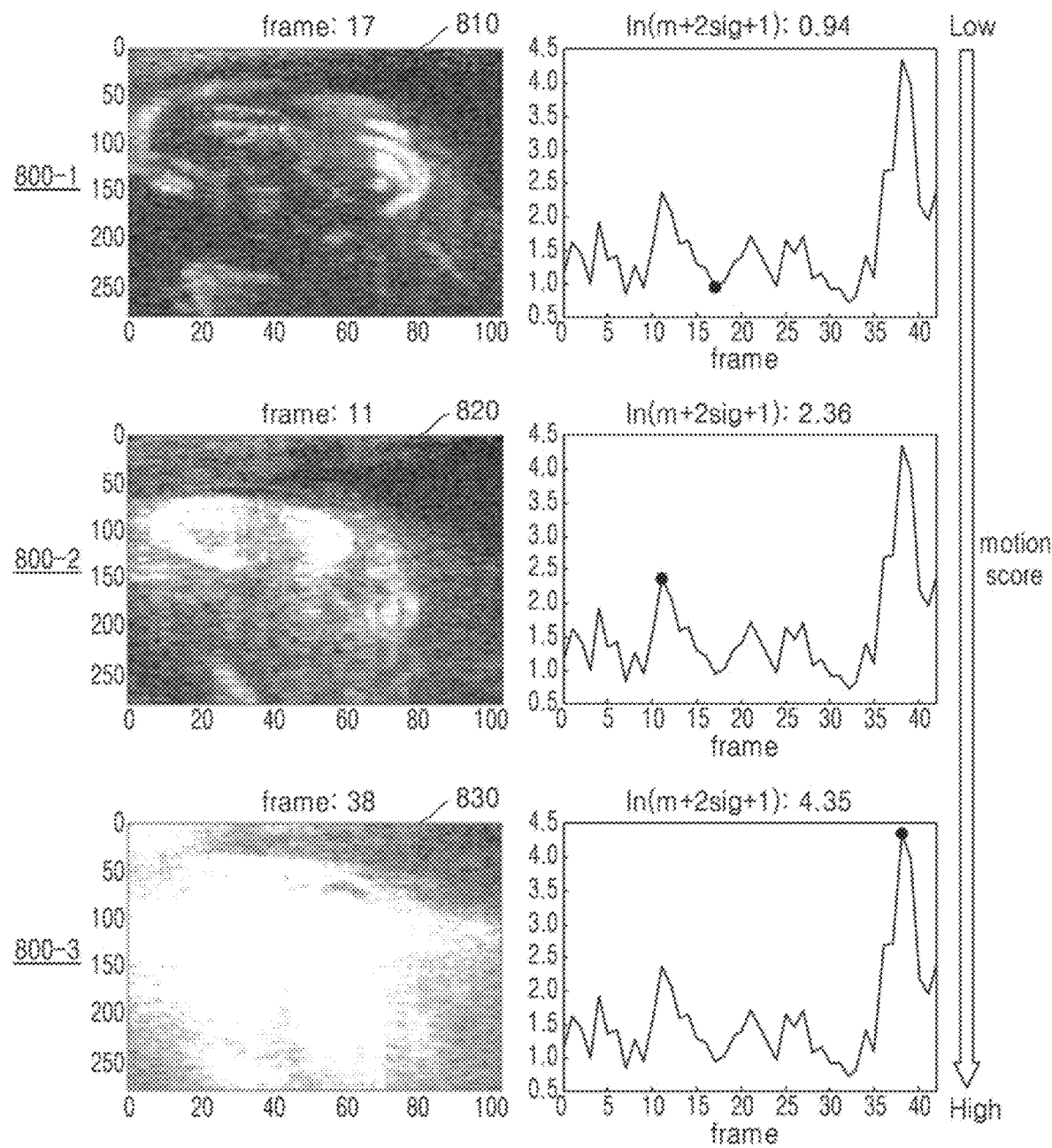
FIG. 8 is a diagram for explaining a relationship between flash artifacts and a motion score, according to an embodiment.

FIG. 8 will be described on the assumption that a first motion score is determined by using Equation 5.

$$\text{Motion Score} = \ln(C_1 * m_{vel_C} + C_2 * \sigma_{vel_C} + C_3) \quad (5)$$

Referring to 800-1 of FIG. 8, a first motion score 811 corresponding to a 17$^{th}$ frame 810 may be '0.94'. Referring to 800-2 of FIG. 8, a first motion score 821 corresponding to an 11$^{th}$ frame 820 may be '2.36'. Referring to 800-3 of FIG. 8, a first motion score 831 corresponding to a 38$^{th}$ frame 830 may be '4.35'.

A degree of flash artifact occurrence of the 11$^{th}$ frame 822 may be greater than that of the 17$^{th}$ frame 810, and a degree of flash artifact occurrence of the 38$^{th}$ frame 830 may be greater than that of the 11$^{th}$ frame 820. Accordingly, referring to FIG. 8, it is found that as a first motion score increases as a degree of flash artifact occurrence increases.

Referring back to FIG. 5, the ultrasound diagnosis apparatus 100 may determine a first weight for suppressing flash artifacts of each pixel by using a CDD described with reference to FIG. 6 and a first motion score described with reference to FIG. 7. The ultrasound diagnosis apparatus 100 may generate a Doppler image 500 from which flash artifacts are suppressed by suppressing flash artifacts of each pixel by applying the first weight to each pixel. For example, the ultrasound diagnosis apparatus 100 may determine the first weight by referring to tables of FIGS. 9A and 9B.

FIGS. 9A and 9B are tables for determining a weight for suppressing flash artifacts of each pixel according to an embodiment.

Referring to FIG. 9A, a degree of flash artifact occurrence (flash degree) 910 may be divided into, but is not limited to, a weak flash 911, a medium flash 912, and a strong flash 913. For example, the ultrasound diagnosis apparatus 100 may identify the flash degree 910 as the weak flash 911 when a first motion score 920 is less than 1, may identify the flash degree 910 as the medium flash 912 when the first motion score 920 is a value between 1 and 3, and may identify the flash degree 910 as the strong flash 913 when the first motion score 920 is greater than 3.

Referring to FIG. 9A, a velocity difference value (e.g., a CDD) between the first Doppler signal 410 and the second Doppler signal 420 may be divided into, but is not limited to, a low CDD 931, a middle CDD 932, and a high CDD 933. For example, the low CDD 931 may correspond to a case where the CDD is less than 0.1, the middle CDD 932 may correspond to a case where the CDD is between 0.1 and 0.6, and the high CDD 933 may correspond to a case where the CDD is greater than 0.6.

According to an embodiment, the ultrasound diagnosis apparatus 100 may determine a first weight 930 based on the first motion score 920 and the CDD.

For example, when the first motion score 920 is 0.94, the ultrasound diagnosis apparatus 100 may identify the flash degree 910 as the weak flash 911. In this case, the first weight 930 of a first pixel having the low CDD 931 where the CDD is 0.01 may be determined to be '0.013', the first weight 930 of a second pixel having the middle CDD 932 where the CDD is 0.5 may be determined to be '0.521', and the first weight 930 of a third pixel having the high CDD 933 where the CDD is 0.8 may be determined to be '0.810'.

Also, when the first motion score 920 is 2.36, the ultrasound diagnosis apparatus 100 may identify the flash degree 910 as the medium flash 912. In this case, the first weight 930 of the first pixel having the low CDD 931 where the CDD is 0.01 may be determined to be '$1.9e^{-05}$(=0.0000095), the first weight 930 of the second pixel having the middle CDD 932 where the CDD is 0.5 may be determined to be '0.194', and the first weight 930 of the third pixel having the high CDD 933 where the CDD is 0.8 may be determined to be '0.590'.

When the first motion score 920 is 4.35, the ultrasound diagnosis apparatus 100 may identify the flash degree 910 as the strong flash 913. In this case, the first weight 930 of the first pixel having the low CDD 931 where the CDD is 0.01 may be determined to be '$2.0e^{-09}$(=0.000000018)', the first weight 930 of the second pixel having the middle CDD 932 where the CDD is 0.5 may be determined to be '0.049', and the first weight 930 of the third pixel having the high CDD 933 where the CDD is 0.8 may be determined to be '0.590'.

Accordingly, according to an embodiment, the ultrasound diagnosis apparatus 100 may determine the first weight so that the first weight of a pixel having the same CDD decreases as the first motion score increases.

Referring to FIG. 9B, when the velocity difference value CDD between the first Doppler signal 410 and the second Doppler signal 420 is greater than a threshold value (e.g., 0.7), the ultrasound diagnosis apparatus 100 may determine that the first weight 930 is '1' irrespective of the first motion score 920. For example, the ultrasound diagnosis apparatus 100 may identify the third pixel having the CDD of 0.8 as a blood flow component, and may determine that the first weight 930 of the third pixel is '1' even when the first motion score 920 is 0.94, may determine that the first weight 930 of the third pixel is '1' even when the first motion score 920 is 2.36, and may determine that the first weight 930 of the third pixel is '1' even when the first motion score 920 is 4.35.

Tables for determining the first weight 930 of FIGS. 9A and 9B are just examples, and thus the present disclosure is not limited thereto.

Figure 10:
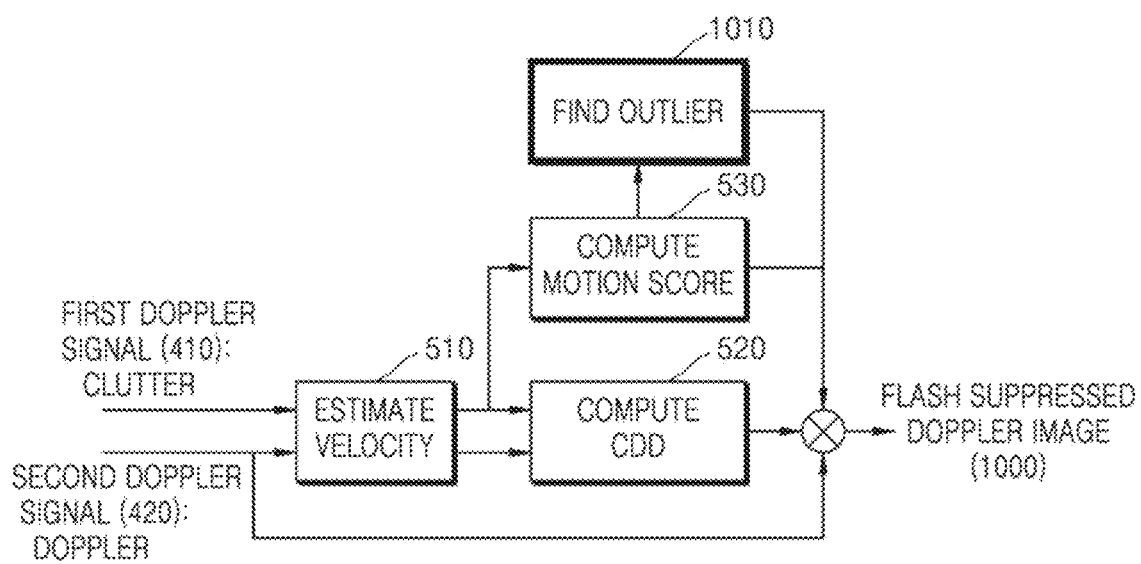
FIG. 10 is a diagram for explaining an operation of determining an outlier based on a velocity value of a first Doppler signal where clutter filtering is not performed, according to an embodiment.

FIG. 10 is a diagram for explaining an operation of determining an outlier based on a velocity value of a first Doppler signal where clutter filtering is not performed according to an embodiment.

According to an embodiment, the ultrasound diagnosis apparatus 100 may determine first pixels for which a velocity value of the first Doppler signal 410 where clutter filtering is not performed is greater than a threshold value (hereinafter, referred to as a 'threshold value for determining an outlier' or a 'threshold value for determining an application range of an algorithm for suppressing flash artifacts') as outliers [1010]. The ultrasound diagnosis apparatus 100 may generate a Doppler image 1000 by applying the algorithm for suppressing flash artifacts to pixels other than the first pixels determined as outliers from among a plurality of pixels. The outliers may include blood flow components having a low CDD.

According to an embodiment, the ultrasound diagnosis apparatus 100 may determine the threshold value for determining an outlier based on a first motion score. For example, the ultrasound diagnosis apparatus 100 may determine the threshold value by using Equation 6.

$$\text{threshold} = C*(\text{Motion Score})) = \qquad (6)$$
$$(m_{vel_C} + 2\sigma_{vel_C}) \text{ OR } = (m_{vel_C} + 5\sigma_{vel_C})$$

Accordingly, according to an embodiment, the threshold value for determining an outlier may increase as the first motion score increases. An outlier will now be described in more detail with reference to FIGS. 11 and 12.

Figure 11:
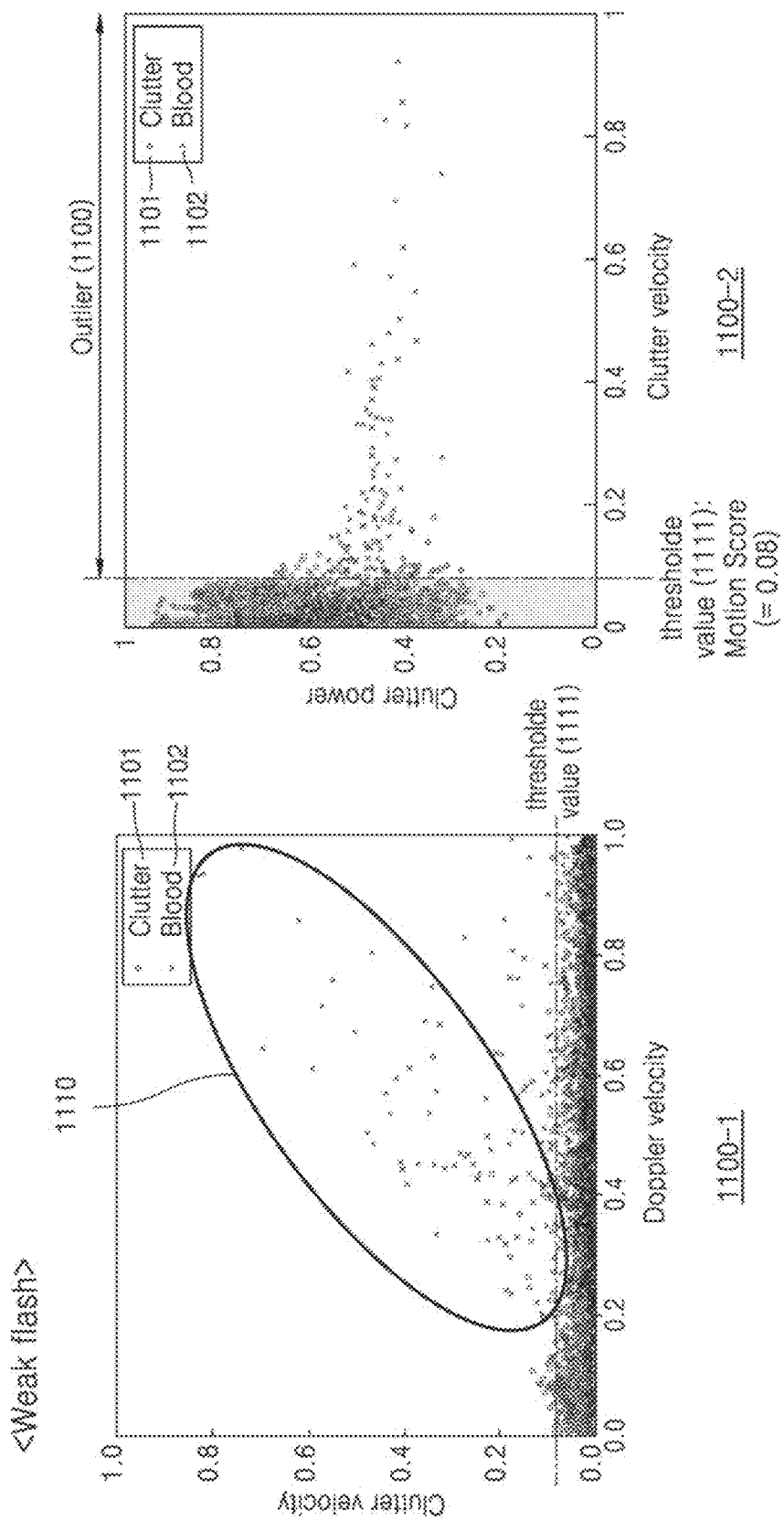
FIG. 11 is a diagram for explaining an operation of determining an application range of an algorithm for suppressing flash artifacts when a degree of flash artifact occurrence is weak.

FIG. 11 is a diagram for explaining an operation of determining an application range of an algorithm for suppressing flash artifacts when a degree of flash artifact occurrence is weak.

Referring to 1100-1 of FIG. 11, when a flash is a weak flash, many blood flow components 1102 having a low CDD may exist in a diagonal area 1110. When a CDD is low, a first weight may be determined to be low. Accordingly, when an algorithm for suppressing flash artifacts is applied even to the blood flow components 1102 included in the diagonal area 1110, not only clutter components 1101 having a low CDD but also the blood flow components 1102 having a low CDD may not be shown in a Doppler image.

Referring to 1100-2 of FIG. 11, in order to prevent pixels of the blood flow components 1102 having a low CDD from being lost, the ultrasound diagnosis apparatus 100 may determine pixels of components having a velocity value greater than a threshold value 1111 may be determined as outliers 1100. In this case, the threshold value 1111 may be a first motion score, for example, 0.08. Accordingly, the ultrasound diagnosis apparatus 100 may classify pixels for which a velocity value of the first Doppler signal 410 is greater than 0.08 as the outliers 1100, and may apply a weight only to pixels for which a velocity value of the first Doppler signal 410 is equal to or less than 0.08.

Figure 12:
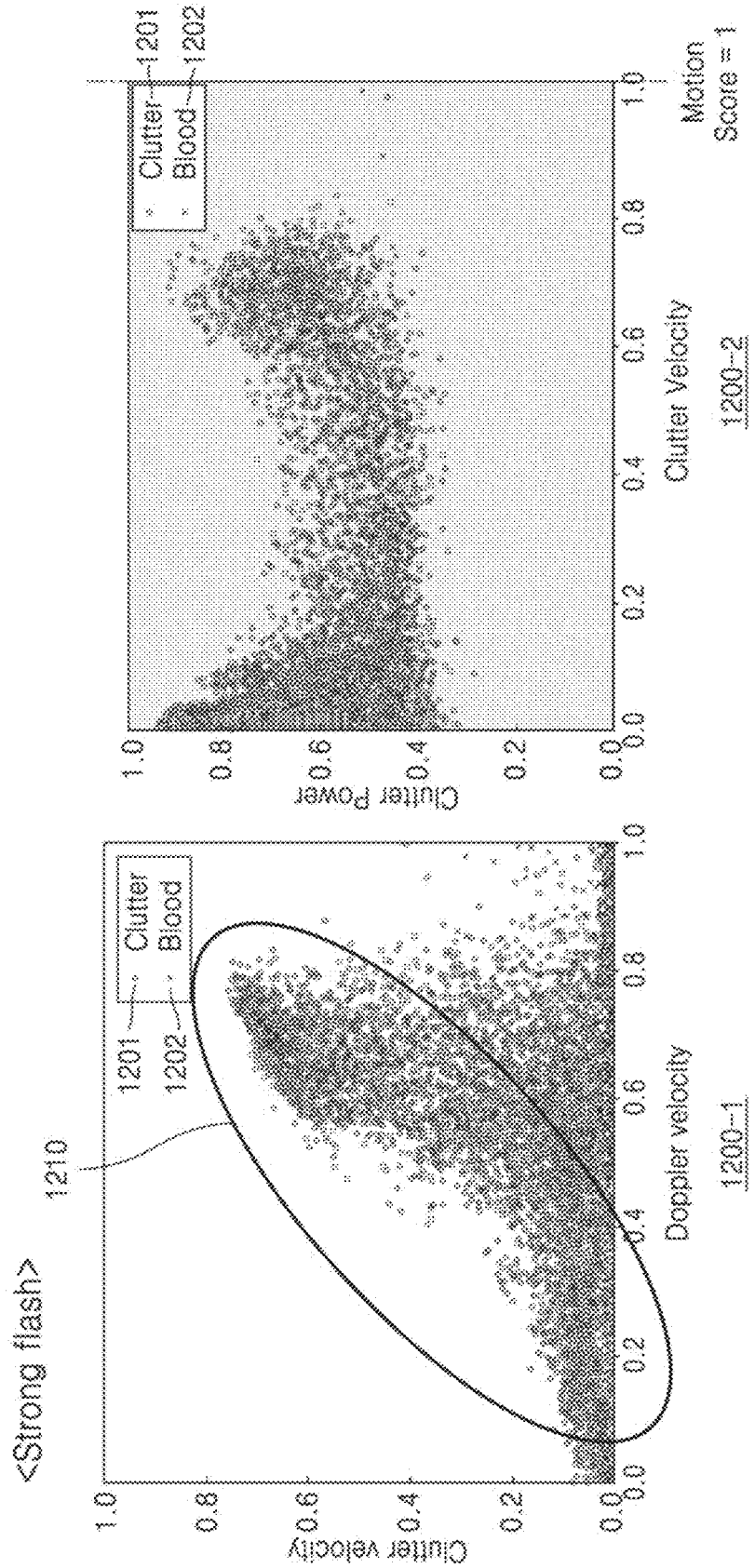
FIG. 12 is a diagram for explaining an operation of determining an application range of an algorithm for suppressing flash artifacts when a degree of flash artifact occurrence is strong.

FIG. 12 is a diagram for explaining an operation of determining an application range of an algorithm for suppressing flash artifacts when a degree of flash artifact occurrence is strong.

Referring to 1200-1 of FIG. 12, when a flash is a strong flash, much more clutter components 1201 having a low CDD than blood flow components 1202 having a low CDD are included in a diagonal area 1210. Accordingly, the ultrasound diagnosis apparatus 100 may extend an application range of an algorithm for suppressing flash artifacts by increasing a threshold value for determining an outlier.

For example, referring to 1200-2 of FIG. 12, the ultrasound diagnosis apparatus 100 may determine the threshold value for determining an outlier (i.e., a threshold value for determining the application range of the algorithm for suppressing flash artifacts) as a first motion score, and the first motion score may be '1'. Accordingly, the ultrasound diagnosis apparatus 100 may apply the algorithm for suppressing flash artifacts to pixels (i.e., all pixels) for which a velocity value of the first Doppler signal 410 is equal to or less than 1.

According to an embodiment, when a flash is a strong flash, since the effect of flash artifacts is so great that, even when some of the blood flow components 1202 having a low CDD are lost, the ultrasound diagnosis apparatus 100 may obtain a high-quality Doppler image by extending the application range of the algorithm for suppressing flash artifacts.

Figure 13:
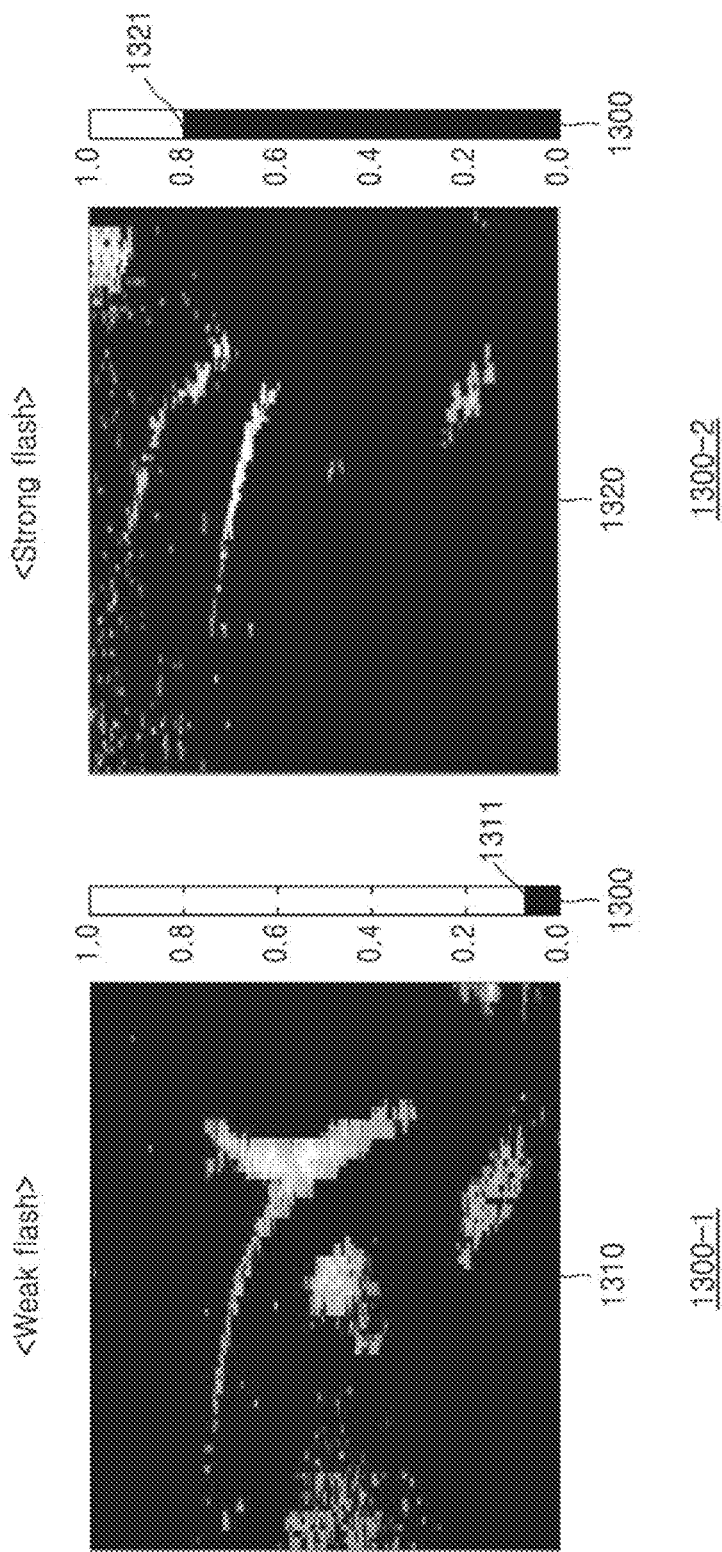
FIG. 13 is a view for explaining an operation of displaying a Doppler image along with a motion score, according to an embodiment.

FIG. 13 is a view for explaining an operation of displaying a Doppler image along with a motion score according to an embodiment.

Referring to 1300-1 of FIG. 13, the ultrasound diagnosis apparatus 100 may display a first Doppler image 1310 from which flash artifacts are suppressed along with a first motion score 1311 corresponding to the first Doppler image 1310. For example, when the first motion score 1311 is 0.08, the ultrasound diagnosis apparatus 100 may display a height corresponding to the first motion score 1311 on a vertical bar 1300 along with the first Doppler image 1310. A user may check an initial degree of flash artifact occurrence before flash artifacts are suppressed through the vertical bar 1300. For example, the user may determine that a degree of flash artifact occurrence is weak since the first motion score 1311 is '0.08'.

Referring to 1300-2 of FIG. 13, the ultrasound diagnosis apparatus 100 may display a second Doppler image 1320 from which flash artifacts are suppressed along with a first motion score 1321 corresponding to the second Doppler image 1320. For example, when the first motion score 1321 is 0.8, the ultrasound diagnosis apparatus 100 may display a height corresponding to the first motion score 1321 on the vertical bar 1300 along with the second Doppler image 1320. In this case, the user may check the initial degree of flash artifact occurrence before flash artifacts are suppressed through the vertical bar 1300. For example, the user may determine that the degree of flash artifact occurrence is strong because the first motion score is '0.8'.

Although the first motion scores 1311 and 1321 are displayed on the vertical bar 1300 in FIG. 13, the present disclosure is not limited thereto. The ultrasound diagnosis apparatus 100 may display the first motion score in any of various ways.

Figure 14:
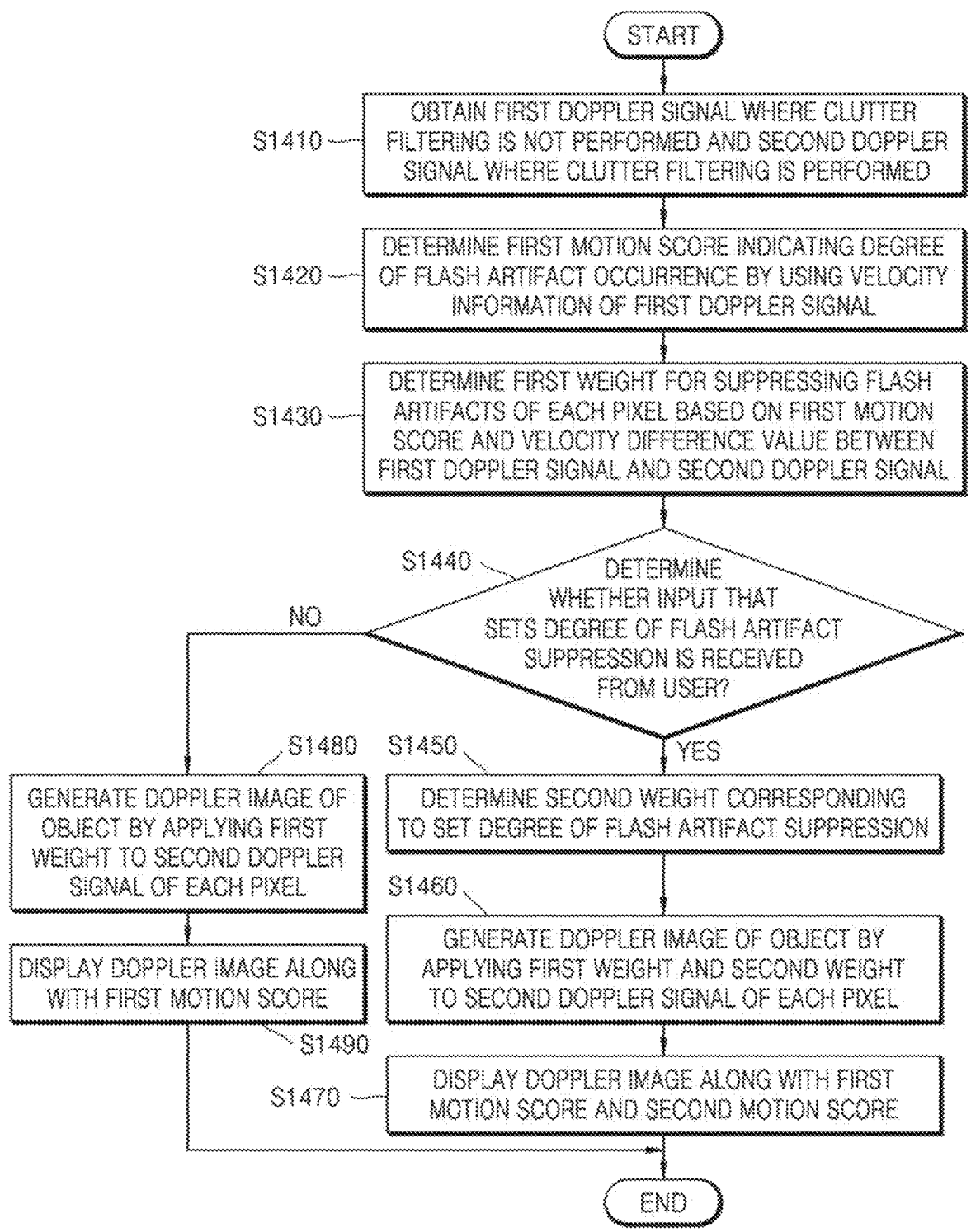
FIG. 14 is a flowchart of a method of displaying a Doppler image based on an input that sets a degree of flash artifact suppression, according to an embodiment.

FIG. 14 is a flowchart of a method of displaying a Doppler image based on an input that sets a degree of flash artifact suppression according to an embodiment.

In operation S1410, the ultrasound diagnosis apparatus 100 may obtain the first Doppler signal 410 where clutter filtering is not performed and the second Doppler signal 420 where clutter filtering is performed. According to an embodiment, the ultrasound diagnosis apparatus 100 may obtain the first Doppler signal 410 and the second Doppler signal 420 corresponding to each of a plurality of pixels.

In operation S1420, the ultrasound diagnosis apparatus 100 may determine a first motion score indicating a degree of flash artifact occurrence by using velocity information of the first Doppler signal 410. The velocity information may include, but is not limited to, a mean velocity of the first Doppler signal 410 where clutter filtering is not performed and a velocity standard deviation of the first Doppler signal 410 where clutter filtering is not performed.

Operations S1410 through S1420 respectively correspond to operations S310 through S320 of FIG. 3, and thus a repeated explanation thereof will not be given.

In operation S1430, the ultrasound diagnosis apparatus 100 may determine a first weight for suppressing flash artifacts of each pixel based on the first motion score and a velocity difference value between the first Doppler signal 410 and the second Doppler signal 420. According to an embodiment, the first weight may be a value between, but not limited to, 0 and 1. An operation by which the ultrasound diagnosis apparatus 100 determines the first weight has been described in detail in operation S330 of FIG. 3, and thus a repeated explanation thereof will not be given.

In operation S1440, the ultrasound diagnosis apparatus 100 may determine whether an input that sets a degree of flash artifact suppression is received from a user. For example, the ultrasound diagnosis apparatus 100 may detect an input event that sets the degree of flash artifact suppression.

According to an embodiment, the ultrasound diagnosis apparatus 100 may receive the input that sets the degree of flash artifact suppression in any of various ways. For example, the ultrasound diagnosis apparatus 100 may receive the input that sets the degree of flash artifact suppression through a GUI displayed on a touchscreen, or may receive the input that sets the degree of flash artifact suppression through a hardware button located on a control panel.

According to an embodiment, the degree of flash artifact suppression may be a value between, but not limited to, 0% and 100%. For example, when the user wants to suppress flash artifacts in a Doppler image as much as possible, the user may input the degree of flash artifact suppression as 100%. In contrast, when the user wants to check a Doppler image where no blood flow component pixels are lost, the user may input the degree of flash artifact suppression as 0%. Also, the user may obtain a desirable Doppler image by appropriately setting the degree of flash artifact suppression.

When the user wants to compare a plurality of Doppler images with different degree of flash artifact suppressions, the user may set the degree of flash artifact suppression in any of various ways. For example, the user may firstly input the degree of flash artifact suppression as 30%, may secondly input the degree of flash artifact suppression as 50%, and may thirdly input the degree of flash artifact suppression as 70%. In this case, the ultrasound diagnosis apparatus 100 may simultaneously display a first Doppler image from which flash artifacts are suppressed by 30%, a second Doppler image from which flash artifacts are suppressed by 50%, and a third Doppler image from which flash artifacts are suppressed by 70%.

In operation S1450, the ultrasound diagnosis apparatus 100 may determine a second weight corresponding to the degree of flash artifact suppression set by the user. For example, the ultrasound diagnosis apparatus 100 may determine the second weight to decrease as the suppress degree set by the user increases, and may determine the second weight to increase as the degree of flash artifact suppression set by the user decreases. According to an embodiment, the second weight may be a value between, but not limited to, 0 and 1.

In operation S1460, the ultrasound diagnosis apparatus 100 may generate a Doppler image of an object by applying the first weight and the second weight to the second Doppler signal of each pixel. For example, the ultrasound diagnosis apparatus 100 may determine a final weight by multiplying the first weight by the second weight, and may apply the determined final weight to the second Doppler signal of each pixel. Accordingly, the final weight may decrease as the degree of flash artifact suppression set by the user increases, and may increase as the degree of flash artifact suppression set by the user decreases. The final weight will now be described in more detail with reference to a table of FIG. 15.

FIG. 15 is a table for determining a weight for suppressing flash artifacts of each pixel based on an input that sets a degree of flash artifact suppression according to an embodiment.

Referring to FIG. 15, a degree of flash artifact occurrence (flash degree) 1510 may be divided into, but is not limited to, a weak flash 1511, a medium flash 1512, and a strong flash 1513. Also, a velocity difference value (e.g., a CDD) between the first Doppler signal 410 and the second Doppler signal 420 may be divided into, but is not limited to, a low CDD 1531, a middle CDD 1532, and a high CDD 1533.

According to an embodiment, the ultrasound diagnosis apparatus 100 may determine a first weight 1530 based on a first motion score 1520 and the CDD. For example, when the first motion score 1520 is 0.94, the ultrasound diagnosis apparatus 100 may identify the flash degree 1510 as the weak flash 1511. In this case, the first weight 1530 of a first pixel having the low CDD 1531 where the CDD is 0.01 may be determined to be '0.013', the first weight 1530 of a second pixel having the middle CDD 1532 where the CDD is 0.5 may be determined to be '0.521', and the first weight 1530 of a third pixel having the high CDD 1533 where the CDD is 0.8 may be determined to be '0.810'.

The ultrasound diagnosis apparatus 100 may determine a second weight 1540 by using, but not limited to, Equation 7.

$$\text{Second weight (alpha)} = 1/\text{suppression degree} \quad (7)$$

For example, the ultrasound diagnosis apparatus 100 may determine that the second weight 1540 is 1 when the degree of flash artifact suppression input from the user is 100% (1541), and may determine that the second weight 1540 is '2(=1/0.5)' when the degree of flash artifact suppression input from the user is 50% (1542).

According to an embodiment, the ultrasound diagnosis apparatus 100 may determine a final weight by multiplying the first weight 1530 by the second weight 1540. According to an embodiment, when a value obtained by multiplying the first weight 1530 by the second weight 1540 exceeds 1, the ultrasound diagnosis apparatus 100 may determine that the final weight is '1'.

For example, when the first motion score 1520 is 0.94 and the degree of flash artifact suppression input from the user is 50% (1542), the ultrasound diagnosis apparatus 100 may determine that the final weight of the first pixel having the low CDD 1531 where the CDD is 0.01 is '0.026(=0.013*2)', the final weight of the second pixel having the middle CDD 1532 where the CDD is 0.5 is '1', and the final weight of the third pixel having the high CDD 1533 where the CDD is 0.8 is '1'. Since a value obtained by multiplying the first weight (0.521) by the second weight (2) of the second pixel is '1.042(=0.521*2)' exceeding 1, the final weight of the second pixel may be determined to be 1. Since a value obtained by multiplying the first weight (0.810) by the second weight (2) of the third pixel is also greater than 1, the weight of the third pixel may also be determined to be 1.

Referring back to FIG. 14, in operation S1470, the ultrasound diagnosis apparatus 100 may provide information indicating the degree of flash artifact suppression. For example, the ultrasound diagnosis apparatus 100 may provide the information indicating the degree of flash artifact suppression by displaying the Doppler image along with the first motion score and a second motion score. The second motion score may indicate a degree of remaining flash artifacts after the first weight and the second weight are applied. Accordingly, a difference between the first motion score and the second motion score may correspond to the degree of flash artifact suppression.

Figure 16:
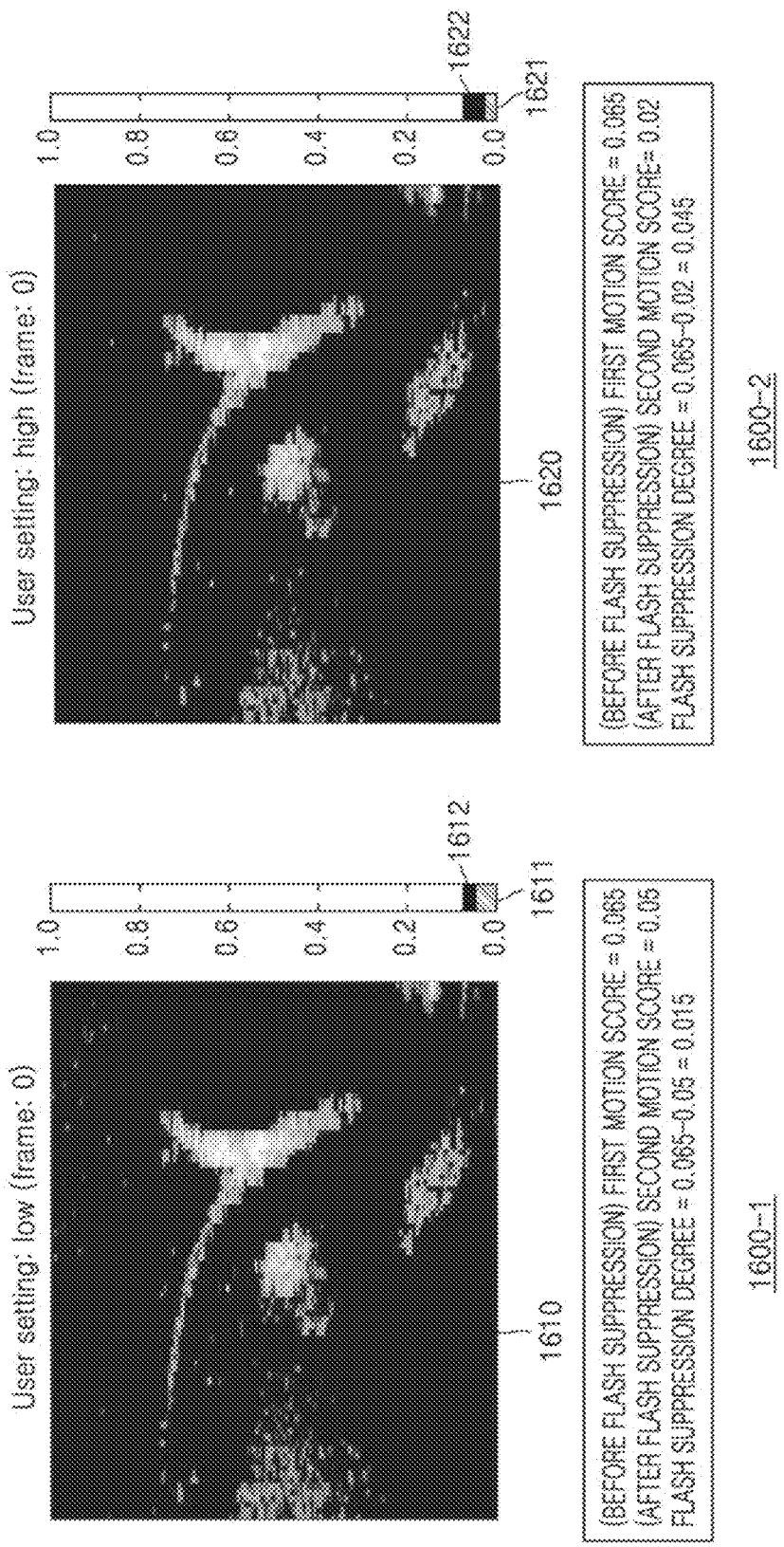
FIG. 16 is a view for explaining an operation by which the ultrasound diagnosis apparatus provides a degree of flash artifact occurrence and a degree of flash artifact suppression along with a Doppler image, according to an embodiment.

For example, referring to FIG. 16, the ultrasound diagnosis apparatus 100 may display the first motion score and the second motion score along with the Doppler image according to the degree of flash artifact suppression set by the user. FIG. 16 will be described on the assumption that the first motion score indicating the degree of flash artifact occurrence is 0.065.

Referring to 1600-1 of FIG. 16, the user may set the degree of flash artifact suppression to 23% that is low. In this case, the second motion score indicating the degree of remaining flash artifacts may be 0.05. The ultrasound diagnosis apparatus 100 may display the first motion score (0.065) and the second motion score (0.05) along with a first Doppler image 1610 from which flash artifacts are suppressed by 23% on a vertical bar 1611. In this case, a difference (0.015) between the first motion score (0.065) and the second motion score (0.05) may correspond to the degree of flash artifact suppression. The ultrasound diagnosis apparatus 100 may display a difference area 1612 between the first motion score and the second motion score in a specific color (e.g., red) on the vertical bar 1611. In this case, the user may intuitively know that the degree of flash artifact suppression is low by rapidly checking the difference area 1612 on the vertical bar 1611.

Referring to 1600-2 of FIG. 16, the user may set the degree of flash artifact suppression to 70% that is high. In this case, the second motion score indicating the degree of remaining flash artifacts may be 0.02. The ultrasound diagnosis apparatus 100 may display the first motion score (0.065) and the second motion score (0.02) along with a second Doppler image 1620 from which flash artifacts are suppressed by 70% on a vertical bar 1621. In this case, a difference (0.045) between the first motion score (0.065) and the second motion score (0.02) may correspond to the degree of flash artifact suppression. The ultrasound diagnosis apparatus 100 may display a difference area 1622 between the first motion score and the second motion score in a specific color (e.g., red) on the vertical bar 1621. In this case, the user may intuitively know that the degree of flash artifact suppression is high by rapidly checking the difference area 1622 on the vertical bar 1621.

Referring back to FIG. 14, when it is determined in operation S1440 that the input that sets the degree of flash artifact suppression is not received from the user, the method proceeds to operation S1480. In operation S1480, the ultrasound diagnosis apparatus 100 may generate the Doppler image of the object by applying the first weight to the second Doppler signal of each pixel.

For example, when the input that sets the degree of flash artifact suppression is not received from the user, the ultrasound diagnosis apparatus 100 may determine that the degree of flash artifact suppression is 100% and the second weight is '1'. In this case, since the final weight obtained by multiplying the first weight by the second weight is the same as the first weight, the ultrasound diagnosis apparatus 100 may generate the Doppler image by applying the first weight to the second Doppler signal of each pixel.

Also, according to an embodiment, when the input that sets the degree of flash artifact suppression is not received from the user, the ultrasound diagnosis apparatus 100 may generate the Doppler image of the object by applying only the first weight to the second Doppler signal of each pixel, without applying the second weight to the second Doppler signal of each pixel.

In operation S1490, the ultrasound diagnosis apparatus 100 may display the Doppler image along with the first motion score. In this case, the first motion score may indicate the degree of flash artifact suppression as well as the degree of flash artifact occurrence. Operation S1490 corresponds to operation S340 of FIG. 3, and thus a detailed explanation thereof will not be given.

An input that sets a degree of flash artifact suppression will now be described in detail with reference to FIGS. 17 through 20.

Figure 17:
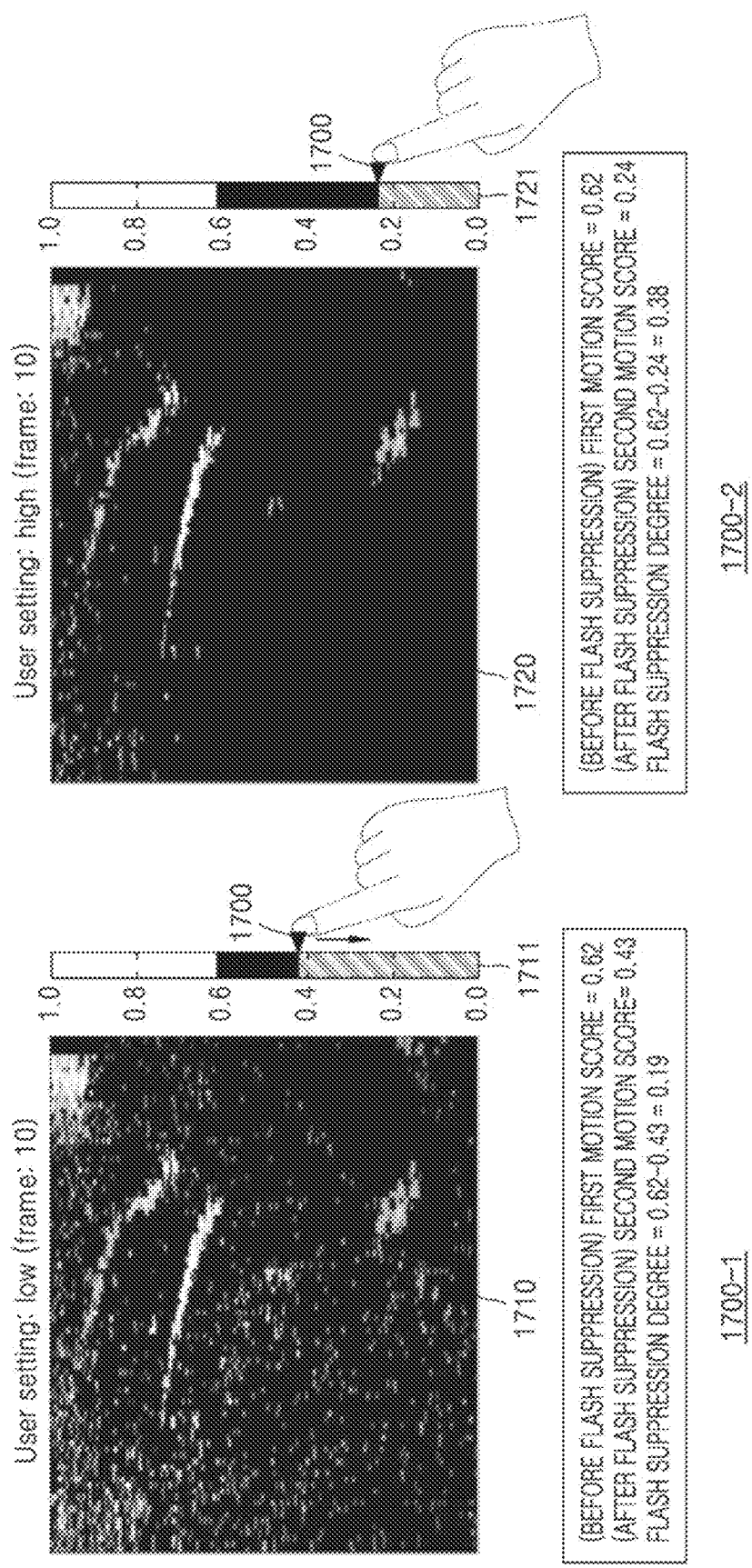
FIG. 17 is a view for explaining a graphical user interface (GUI) for setting a degree of flash artifact suppression, according to an embodiment.

FIG. 17 is a view for explaining a GUI for setting a degree of flash artifact suppression according to an embodiment.

Referring to 1700-1 of FIG. 17, the ultrasound diagnosis apparatus 100 may display an adjustment button 1700 on a vertical bar 1711 indicating a first motion score (0.62) and a second score (0.43). In this case, the adjustment button 1700 may be displayed next to the second motion score (0.43). A user may check that a degree of flash artifact occurrence corresponding to a first Doppler image 1710 is high by using the first motion score (0.62). Also, the user may check that a degree of flash artifact suppression is 'about 30%' by using a length (0.19) between the first motion score (0.62) and the second motion score (0.43). The user may change the degree of flash artifact suppression by vertically adjusting a position of the adjustment button 1700.

Referring to 1700-2 of FIG. 17, the ultrasound diagnosis apparatus 100 may receive a user input that drags the adjustment button 1700 downward while touching the adjustment button 1700. In this case, the ultrasound diagnosis apparatus 100 may increase the degree of flash artifact suppression in response to the user input. For example, the ultrasound diagnosis apparatus 100 may increase the degree of flash artifact suppression from 30% to 61%. When the degree of flash artifact suppression is increased from 30% to 61%, the second motion score indicating a degree of remaining flash artifacts may be reduced from 0.43 to 0.24.

Once the degree of flash artifact suppression is increased, a second Doppler image 1720 may be displayed more clearly than the first Doppler image 1710. Also, a length between the first motion score (0.62) and the second motion score (0.24) of a vertical bar 1721 corresponding to the second Doppler image 1720 may be increased to '0.38'. Accordingly, the user may easily adjust the degree of flash artifact suppression by changing the length between the first motion score and the second motion score.

Figure 18:
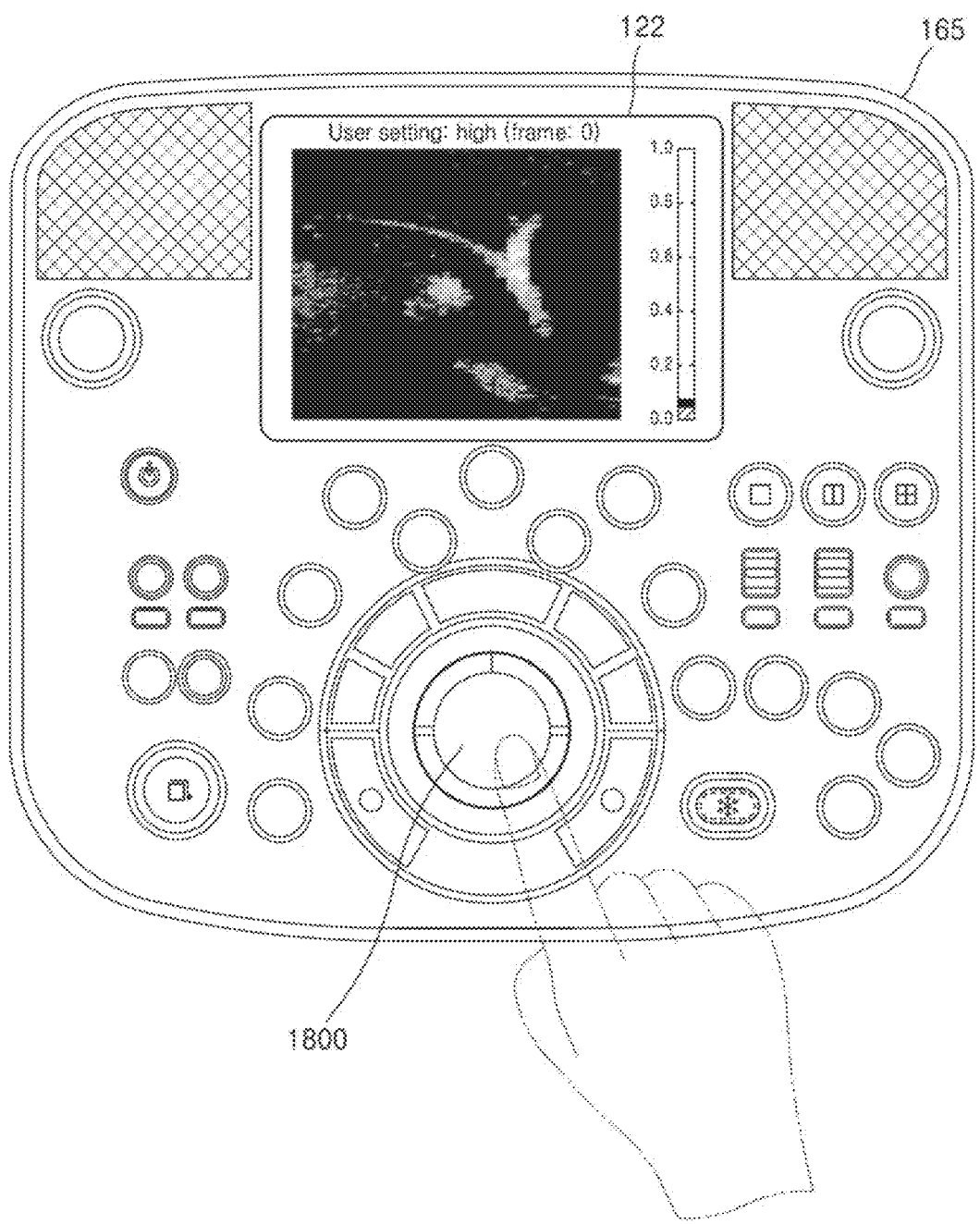
FIG. 18 is a view for explaining an operation of receiving an input that sets a degree of flash artifact suppression by using a trackball, according to an embodiment.

FIG. 18 is a view for explaining an operation of receiving an input that sets a degree of flash artifact suppression by using a trackball according to an embodiment.

According to an embodiment, a user may adjust a trackball 1800 included in a control panel 165 while watching a vertical bar and a Doppler image displayed on a sub-display 122. For example, the user may turn the trackball 1800 rightward in order to increase a degree of flash artifact suppression. In this case, the ultrasound diagnosis apparatus 100 may increase a length (or an area) between a first motion score and a second motion score displayed on the vertical bar, and may display the Doppler image from which flash artifacts are more suppressed.

In contrast, the user may turn the trackball 1800 leftward in order to reduce the degree of flash artifact suppression. In this case, the ultrasound diagnosis apparatus 100 may reduce the length (or the area) between the first motion score and the second motion score displayed on the vertical bar, and may display the Doppler image from which flash artifacts are less suppressed.

Figure 19:
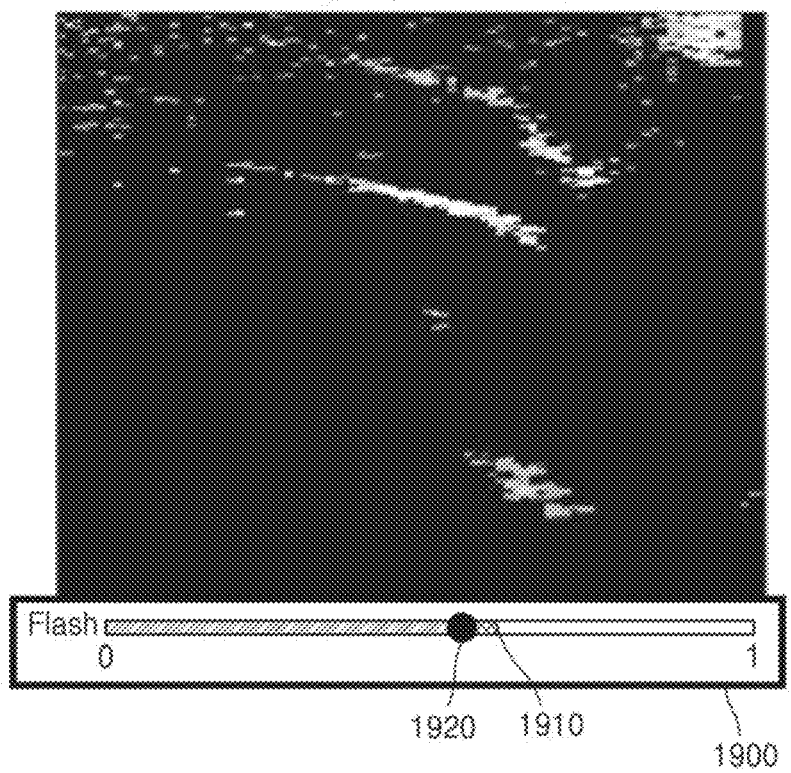
FIG. 19 is a view for explaining a GUI for setting a degree of flash artifact suppression, according to an embodiment.

FIG. 19 is a view for explaining a GUI for setting a degree of flash artifact suppression according to an embodiment.

Referring to FIG. 19, the ultrasound diagnosis apparatus 100 may provide a GUI for setting a degree of flash artifact suppression in the form of a horizontal bar 1900. For example, the ultrasound diagnosis apparatus 100 may display a first motion score 1910 indicating a degree of flash artifact occurrence on the horizontal bar 1900. Also, the ultrasound diagnosis apparatus 100 may display an adjustment button 1920 for adjusting the degree of flash artifact suppression on the horizontal bar 1900. In this case, a position of the adjustment button 1920 may correspond to a second motion score indicating a degree of remaining flash artifacts. A user may easily adjust the degree of flash artifact suppression by horizontally changing the position of the adjustment button 1920.

Figure 20:
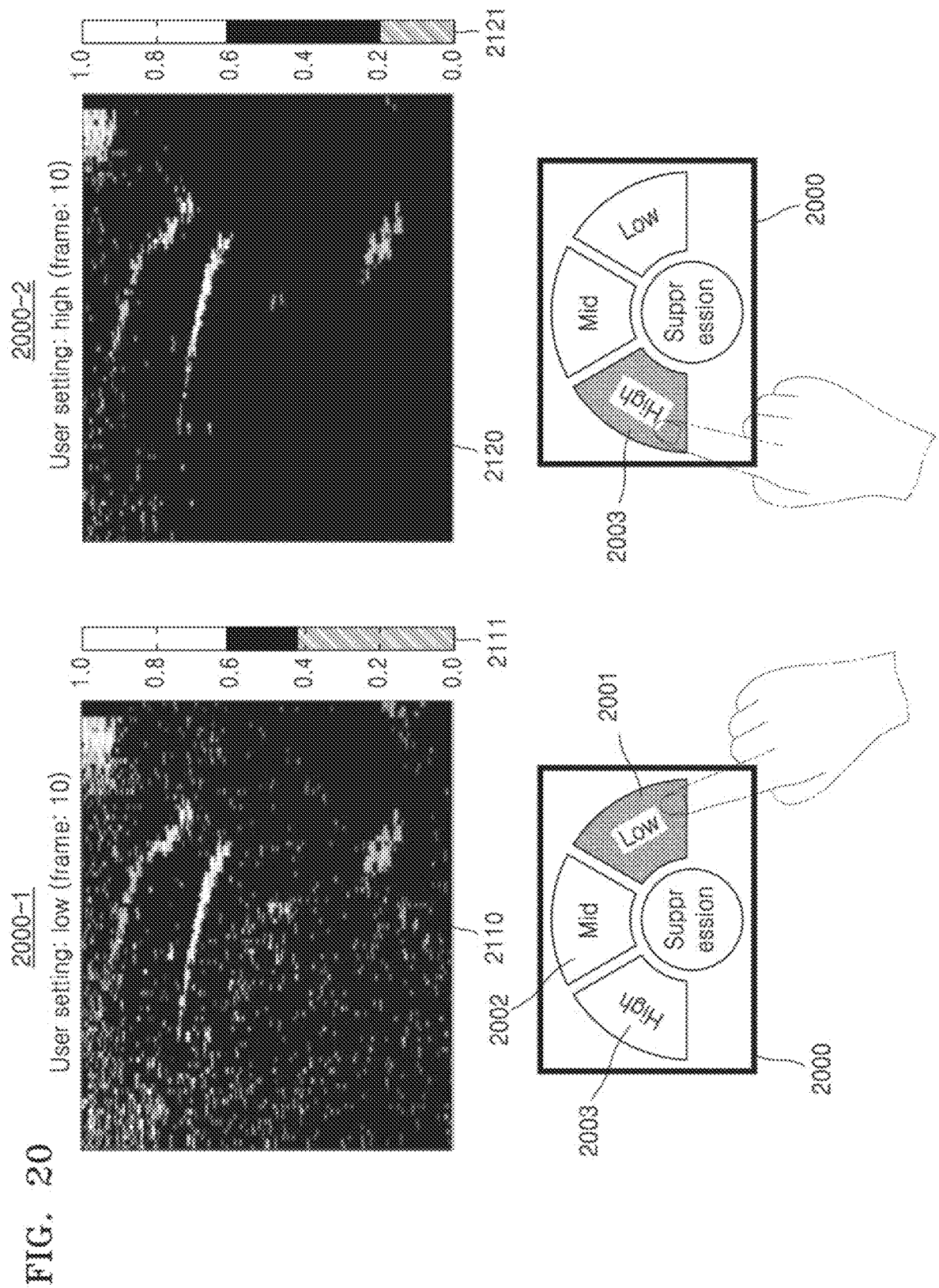
FIG. 20 is a view for explaining a GUI for setting a degree of flash artifact suppression by using a button, according to an embodiment.

FIG. 20 is a view illustrating a GUI for setting a degree of flash artifact suppression by using a button according to an embodiment. FIG. 20 will be described on the assumption that a first motion score indicating a degree of flash artifact occurrence is 0.62.

According to an embodiment, the ultrasound diagnosis apparatus 100 may provide a GUI 2000 including buttons for simply selecting a degree of flash artifact suppression. For example, the GUI 2000 may include, but is not limited to, a low button 2001, a medium button 2002, and a high button 2003.

Referring to 2000-1 of FIG. 20, the ultrasound diagnosis apparatus 100 may receive an input that selects the low button 2001. In this case, the ultrasound diagnosis apparatus 100 may set the degree of flash artifact suppression to 25% that is low, and may display a first Doppler image 2110 from which flash artifacts are suppressed by 25%. Also, the ultrasound diagnosis apparatus 100 may display the degree of flash artifact suppression (25%) next to the first Doppler image 2110. For example, the ultrasound diagnosis apparatus 100 may display an area between a first motion score (0.62) and a second motion score (0.43) in a specific color on a vertical bar 2111. A width of the area displayed in the specific color may correspond to the degree of flash artifact suppression (25%).

Referring to 2000-2 of FIG. 20, the ultrasound diagnosis apparatus 100 may receive an input that selects the high button 2003. In this case, the ultrasound diagnosis apparatus 100 may set the degree of flash artifact suppression to 70% that is high, and may display a second Doppler image 2120 from which flash artifacts are suppressed by 70%. Also, the ultrasound diagnosis apparatus 100 may display the degree of flash artifact suppression (70%) next to the second Doppler image 2120. For example, the ultrasound diagnosis apparatus 100 may display an area between the first motion score (0.62) and the second motion score (0.2) in a specific color on a vertical bar 2121. A width of the area displayed in the specific color may correspond to the degree of flash artifact suppression (70%).

Although the degree of flash artifact suppression is displayed in a specific color on the vertical bards 2111 and 2121 in FIG. 20, the present disclosure is not limited thereto. For example, the ultrasound diagnosis apparatus 100 may display the degree of flash artifact suppression as text. For example, the ultrasound diagnosis apparatus 100 may display the degree of flash artifact suppression as text saying 'suppression degree: 20%'.

The method according to an embodiment may be implemented as computer instructions which may be executed by various computer means, and recorded on a computer-readable recording medium. The computer-readable recording medium may include program commands, data files, data structures, or a combination thereof. The program commands recorded on the computer-readable recording medium may be specially designed and constructed for the present disclosure or may be known to and usable by one of ordinary skill in the field of computer software. Examples of the computer-readable recording medium include storage media such as magnetic media (e.g., hard discs, floppy discs, or magnetic tapes), optical media (e.g., compact disc-read-only memories (CD-ROMs) or digital versatile discs (DVDs)), magneto-optical media (e.g., floptical discs), and hardware devices that are specially configured to store and carry out program commands (e.g., ROMs, random-access memories (RAMs), or flash memories). Examples of the program commands include a high-level language code that may be executed by a computer using an interpreter as well as a machine language code made by a compiler.

While one or more embodiments have been described with reference to the figures, it will be understood by one of ordinary skill in the art that various changes in form and details may be made therein without departing from the spirit and scope of the disclosure as defined by the following claims.

What is claimed is:

1. A method of displaying a Doppler image, the method comprising:

transmitting, by a probe, an ultrasound signal to an object and receiving the ultrasound signal reflected from the object;

generating, by an ultrasound receiver, the reflected ultrasound signal as ultrasound data;

and generating, by an image processing unit, an ultrasound image including a plurality of pixels by using the ultrasound data, wherein the generating, by the ultrasound receiver, the reflected ultrasound signal comprises:

obtaining a first Doppler signal where clutter filtering corresponding to each of the plurality of pixels is not performed and a second Doppler signal where clutter filtering corresponding to each of the plurality of pixels is performed;

determining a first motion score indicating a degree of flash artifact occurrence by using velocity information of the first Doppler signal;

and determining a first weight for suppressing flash artifacts of each pixel based on the first motion score and a velocity difference value between the first Doppler signal and the second Doppler signal, and wherein the generating, by the image processing unit, the ultrasound image comprises:

generating a first Doppler image of the object by applying the first weight to the second Doppler signal of each pixel;

and displaying the first Doppler image of the object, wherein the method further comprises determining a second motion score indicating a degree of remaining flash artifacts after the first weight is applied, and a difference value between the first motion score and the second motion score corresponding to a degree of flash artifact suppression, and wherein the displaying of the first Doppler image comprises displaying the first Doppler image along with the first motion score regardless of a magnitude of the first motion score, the second motion score, and the difference value between the first motion score and the second motion score.

2. The method of claim 1, wherein the velocity information of the first Doppler signal comprises a mean velocity of the first Doppler signal and a velocity standard deviation of the first Doppler signal.

3. The method of claim 1, wherein the determining of the first motion score comprises determining the first motion score by using velocity distribution information of the first Doppler signal having a power greater than a mean power.

4. The method of claim 1, wherein the generating of the Doppler image of the object comprises:
receiving an input that sets a degree of flash artifact suppression from a user;
determining a second weight corresponding to the set degree of flash artifact suppression; and
generating a second Doppler image of the object by applying the first weight and the second weight to the second Doppler signal of each pixel.

5. The method of claim 4, further comprising providing information indicating the degree of flash artifact suppression.

6. The method of claim 5, wherein the providing of the information indicating the degree of flash artifact suppression comprises displaying, along with the first motion score, the second motion score indicating the degree of the remaining flash artifacts after the first weight and the second weight are applied.

7. The method of claim 1, wherein the determining of the first weight comprises determining the first weight to decrease as the first motion score increases.

8. The method of claim 1, wherein the determining of the first weight comprises:
determining first pixels, for which a velocity value of the first Doppler signal is greater than a threshold value, as outliers;
determining pixels other than the first pixels from among the plurality of pixels as second pixels for suppressing the flash artifacts; and
determining the first weight corresponding to each of the second pixels, based on the first motion score and the velocity difference value between the first Doppler signal and the second Doppler signal.

9. The method of claim 1, wherein the determining of the first weight comprises determining that the first weight is 1 when the velocity difference value between the first Doppler signal and the second Doppler signal is greater than a threshold value.

10. A non-transitory computer-readable recording medium having
recorded thereon a program comprising instructions which, when executed by a computer, cause the computer to execute a method including:
controlling a probe to transmit an ultrasound signal to an object and receive the ultrasound signal reflected from the object,
controlling an ultrasound receiver to generate the reflected ultrasound signal as ultrasound data; and
controlling an image processing unit to generate an ultrasound image including a plurality of pixels by using the ultrasound data,
wherein the controlling the ultrasound receiver, to generate the reflected ultrasound signal as the ultrasound data, further includes:
obtaining a first Doppler signal where clutter filtering corresponding to each of the plurality of pixels is not performed and a second Doppler signal where clutter filtering corresponding to each of the plurality of pixels is performed;
determining a first motion score indicating a degree of flash artifact occurrence by using velocity information of the first Doppler signal; and
determining a first weight for suppressing flash artifacts of each pixel based on the first motion score and a velocity difference value between the first Doppler signal and the second Doppler signal,
wherein the controlling the image processing unit to generate the ultrasound image further includes:
generating a first Doppler image of the object by applying the first weight to the second Doppler signal of each pixel; and
displaying the first Doppler image of the object,
wherein the method further comprises determining a second motion score indicating a degree of remaining flash artifacts after the first weight is applied, and a difference value between the first motion score and the second motion score corresponding to a degree of flash artifact suppression, and
wherein the displaying of the first Doppler image comprises displaying the first Doppler image along with the first motion score regardless of a magnitude of the first motion score, the second motion score, and the difference value between the first motion score and the second motion score.

* * * * *